(12) United States Patent
Li et al.

(10) Patent No.: US 10,989,668 B2
(45) Date of Patent: Apr. 27, 2021

(54) METHOD FOR DIRECT OPTICAL VISUALIZATION OF GRAPHENE AND ITS NANOSCALE DEFECTS ON TRANSPARENT SUBSTRATES

(71) Applicant: The Regents of the University of California, Oakland, CA (US)

(72) Inventors: Wan Li, Berkeley, CA (US); Seonah Moon, Berkeley, CA (US); Michal Wojcik, Berkeley, CA (US); Ke Xu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 198 days.

(21) Appl. No.: 16/312,990

(22) PCT Filed: Jun. 27, 2017

(86) PCT No.: PCT/US2017/039411
§ 371 (c)(1),
(2) Date: Dec. 21, 2018

(87) PCT Pub. No.: WO2018/005431
PCT Pub. Date: Jan. 4, 2018

(65) Prior Publication Data
US 2019/0219519 A1    Jul. 18, 2019

Related U.S. Application Data

(60) Provisional application No. 62/355,327, filed on Jun. 27, 2016.

(51) Int. Cl.
*G06K 9/00* (2006.01)
*G01N 21/892* (2006.01)
(Continued)

(52) U.S. Cl.
CPC ............ *G01N 21/892* (2013.01); *B82Y 30/00* (2013.01); *G01N 13/00* (2013.01); *G01N 21/45* (2013.01);
(Continued)

(58) Field of Classification Search
CPC ...... G01N 21/892; G01N 33/00; G01N 13/00; G01N 21/45; G01N 21/8422;
(Continued)

(56) References Cited

U.S. PATENT DOCUMENTS

2012/0021249 A1* 1/2012 Shin ................ B82Y 40/00
428/688
2013/0087705 A1* 4/2013 Hiura ................ G01N 23/2251
250/307

(Continued)

OTHER PUBLICATIONS

Romagnoli et al., "Making graphene visisible on transparent dielectric substrates: Brewster angle imaging," 2D Materials, vol. 2, No. 3, 035017, Sep. 25, 2015. (Year: 2015).*
(Continued)

*Primary Examiner* — Van D Huynh
(74) *Attorney, Agent, or Firm* — Gavrilovich, Dodd & Lindsey LLP

(57) ABSTRACT

The disclosure provides methods for the direct optical visualization of graphene and its nanoscale defects on transparent substrates.

16 Claims, 33 Drawing Sheets

(51) Int. Cl.

| | |
|---|---|
| *B82Y 30/00* | (2011.01) |
| *G01N 21/45* | (2006.01) |
| *G01N 21/84* | (2006.01) |
| *G02B 21/00* | (2006.01) |
| *G02B 21/32* | (2006.01) |
| *G01N 33/00* | (2006.01) |
| *G01N 13/00* | (2006.01) |
| *B82Y 40/00* | (2011.01) |
| *B82Y 35/00* | (2011.01) |

(52) U.S. Cl.
CPC ......... *G01N 21/8422* (2013.01); *G01N 33/00* (2013.01); *G02B 21/0016* (2013.01); *G02B 21/0088* (2013.01); *G02B 21/32* (2013.01); *B82Y 35/00* (2013.01); *B82Y 40/00* (2013.01); *G01N 2021/8427* (2013.01); *G01N 2033/0096* (2013.01)

(58) Field of Classification Search
CPC ... G01N 2021/8427; G01N 2033/0096; G02B 21/0016; G02B 21/0088; G02B 21/32; B82Y 30/00; B82Y 35/00; B82Y 40/00
USPC .......................................................... 382/141
See application file for complete search history.

(56) References Cited

U.S. PATENT DOCUMENTS

| | | | | |
|---|---|---|---|---|
| 2014/0376799 | A1* | 12/2014 | Wang ..................... | G01B 11/06 382/141 |
| 2015/0199826 | A1* | 7/2015 | Jessen ..................... | G06T 7/90 382/103 |
| 2015/0348669 | A1* | 12/2015 | Adamson ................ | C09D 5/24 252/511 |
| 2016/0325580 | A1* | 11/2016 | Farmer ................... | G01N 21/534 |

OTHER PUBLICATIONS

Wiegand et al., "Microinterferometry: three-dimensional reconstruction of surface microtopography for thin-film and wetting studies by reflection interference contrast microscopy (RICM)," Applied Optics, vol. 37, No. 29, pp. 6892-6905, 1998. (Year: 1998).*
Verschueren et al., "Interference reflection microscopy in cell biology: methodology and applications," J. of Cell Sci., vol. 75, No. 1, pp. 279-301, 1985. (Year: 1985).*
Li et al., "Direct optical imagining of graphene in vitro by nonlinear femtosecond laser spectral reshaping," Nano Letters, vol. 12, No. 11, p. 4, Oct. 30, 2012. (Year: 2012).*
Wang, Xin, International Preliminary Report on Patentability and Written Opinion, PCT/US2017/039411, The International Bureau of WIPO, dated Jan. 10, 2019.
Thomas, Shane, International Search Report and Written Opinion, PCT/US2017/039411, United States Patent and Trademark Office, dated Sep. 6, 2017.
Li et al., "Direct optical imagining of graphene in vitro by nonlinear femtosecond laser spectral reshaping," Nano Letters, vol. 12, No. 11, p. 4, Oct. 30, 2012.
Li et al., "Direct Optical Visualization of Graphene and Its Nanoscale Defects on Transparent Substrates," Nano Letters, vol. 16, No. 8, pp. 5027-5031, Jun. 28, 2016.
Romagnoli et al., "Making graphene visisible on transparent dielectric substrates: Brewster angle imaging," 2D Materials, vol. 2, No. 3, 035017, Sep. 25, 2015.
Verschueren et al., "Interference reflection microscopy in cell biology: methodology and applications," J. of Cell Sci., vol. 75, No. 1, pp. 279-301, 1985.
Wiegand et al., "Microinterferometry: three-dimensional reconstruction of surface microtopography for thin-film and wetting studies by reflection interference contrast microscopy (RICM)," Applied Optics, vol. 37, No. 29, pp. 6892-6905, 1998.

* cited by examiner

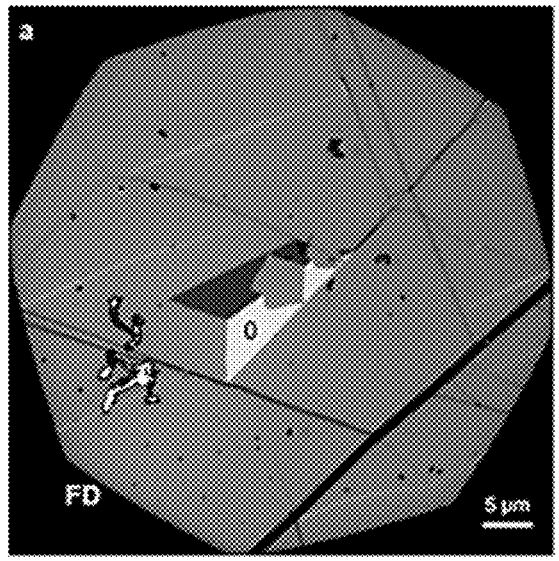
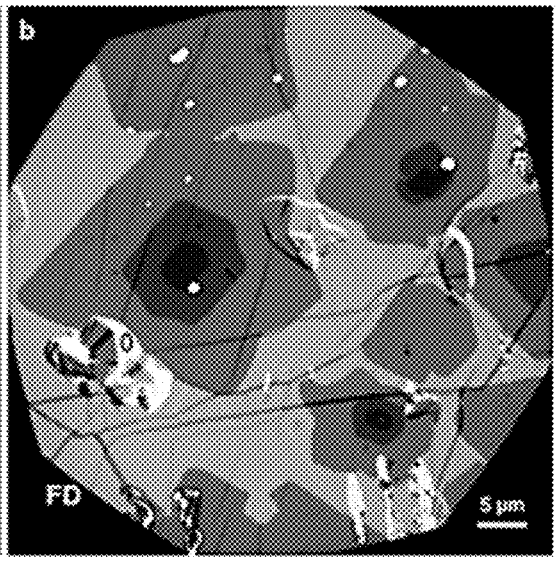
FIG. 11A          FIG. 11B
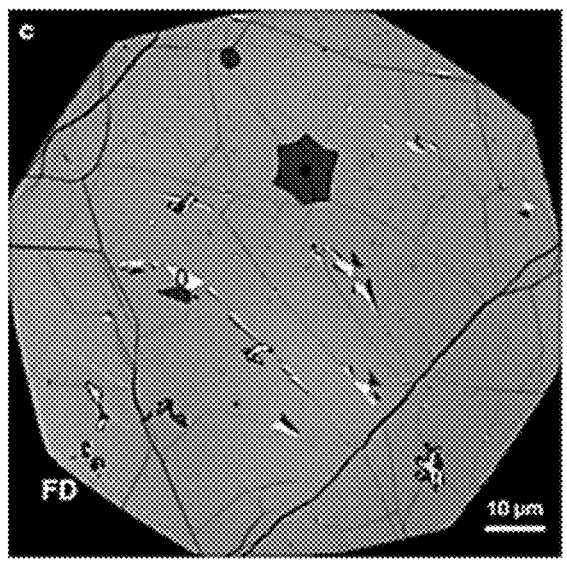
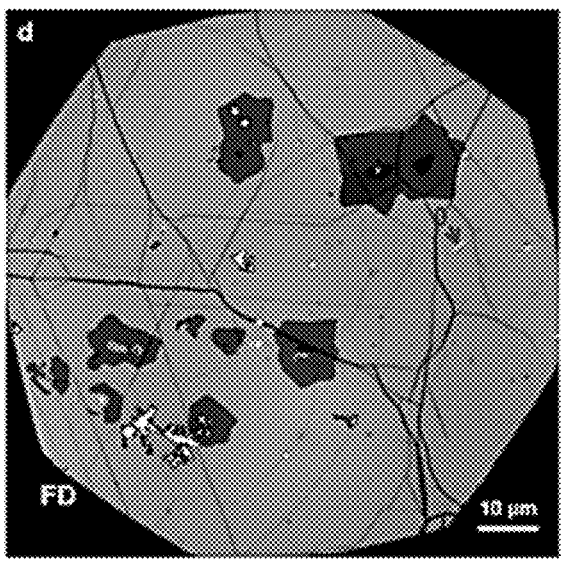
FIG. 11C          FIG. 11D

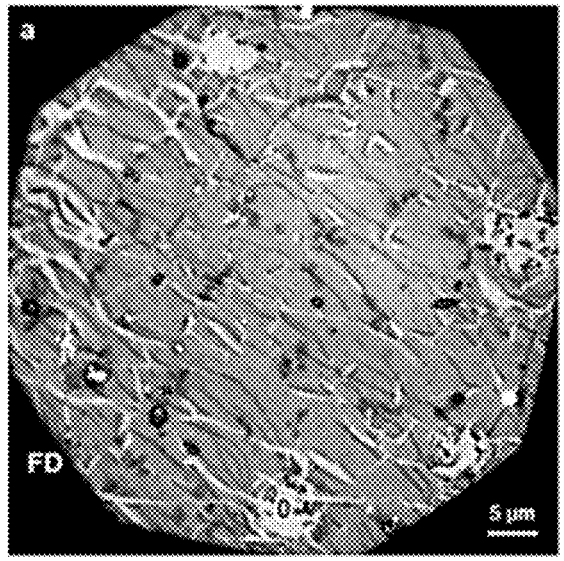
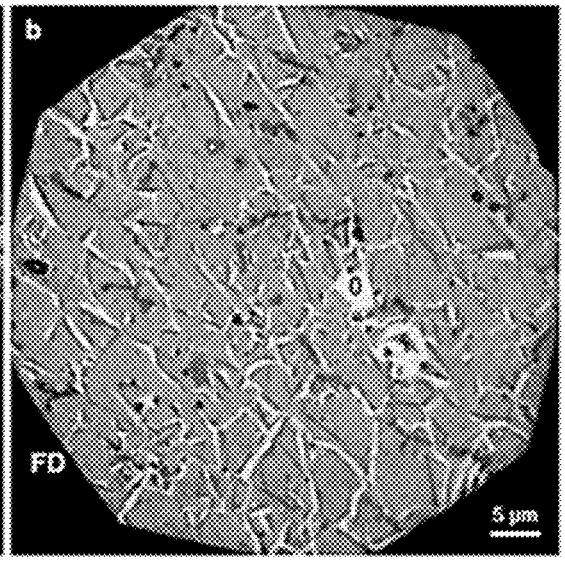
FIG. 18A  FIG. 18B
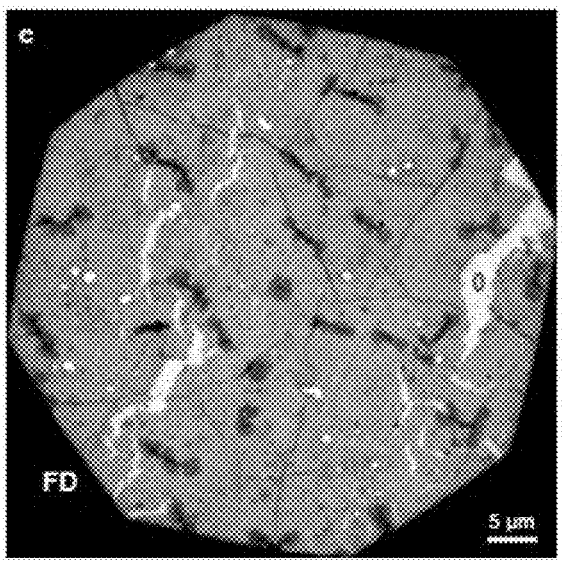
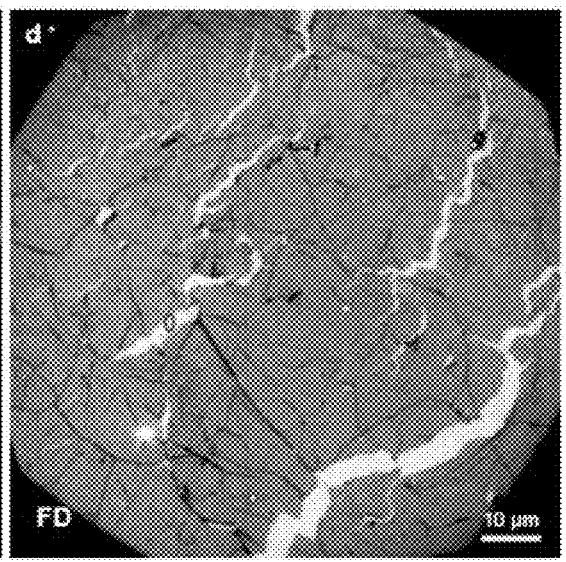
FIG. 18C  FIG. 18D

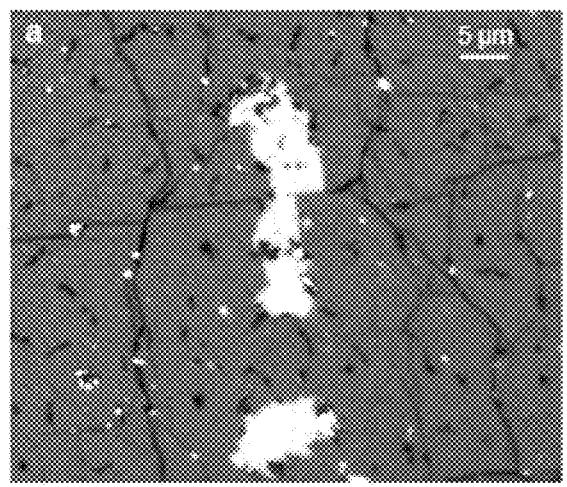
*FIG. 19A*
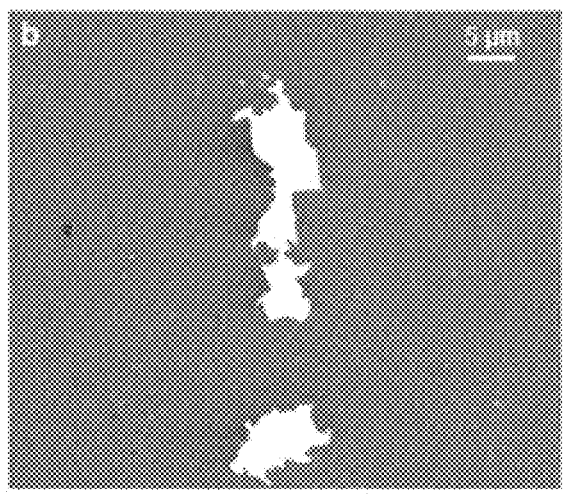 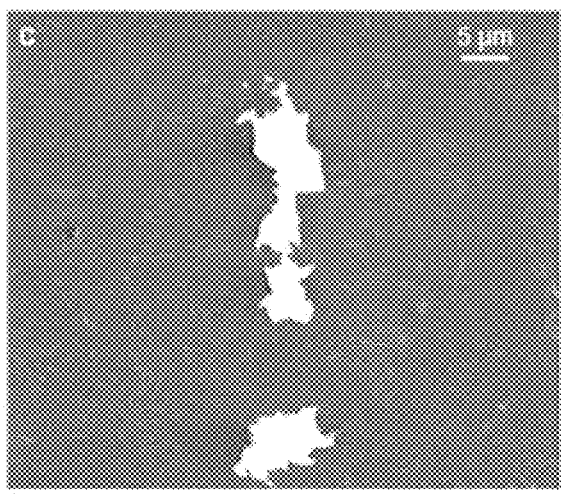
*FIG. 19B*  *FIG. 19C*

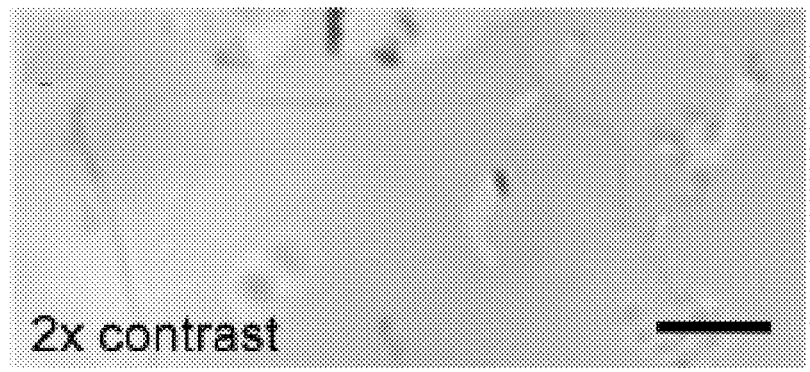
FIG. 21E
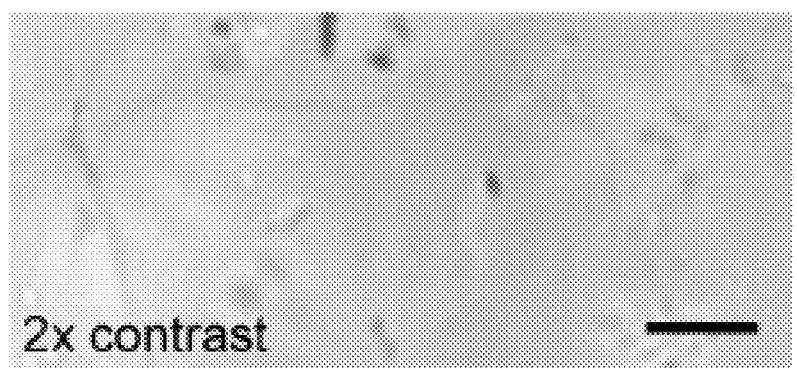
FIG. 21F
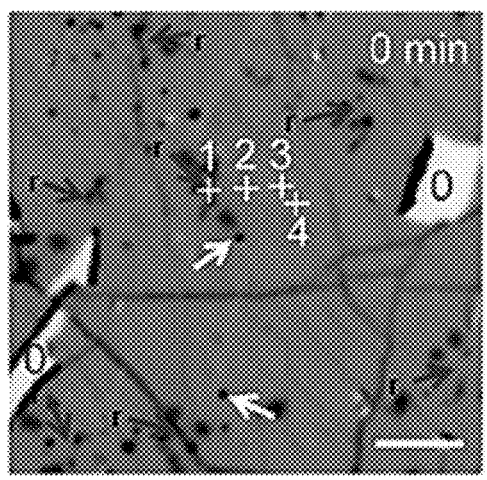 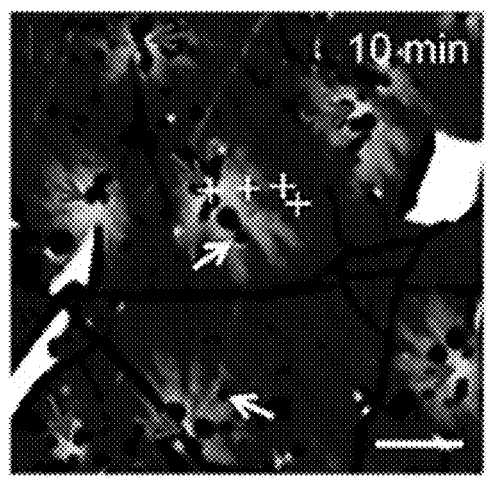
FIG. 22A    FIG. 22B

METHOD FOR DIRECT OPTICAL VISUALIZATION OF GRAPHENE AND ITS NANOSCALE DEFECTS ON TRANSPARENT SUBSTRATES

CROSS REFERENCE TO RELATED APPLICATIONS

This application is a U.S. National Stage Application filed under 35 U.S.C. § 371 and claims priority from International Application No. PCT/US2017/039411, filed Jun. 27, 2017, which application claims priority under 35 U.S.C. § 119 from Provisional Application Ser. No. 62/355,327 filed Jun. 27, 2016, the disclosures of which are incorporated herein by reference.

TECHNICAL FIELD

The disclosure provides methods for the direct optical visualization of graphene and its nanoscale defects on transparent substrates.

BACKGROUND

Graphene, a single layer of bonded carbon atoms and a rising two-dimensional material, possesses outstanding electrical, optical, and mechanical properties and thus great commercial values. In particular, the high electrical conductivity and low light absorption (2.3%) of graphene, combined with its excellent mechanical strength and flexibility, chemical stability, and low contact resistance to organic materials, offer tremendous advantages as transparent and flexible electrode materials in applications ranging from solar cells, organic emitting diodes, liquid crystal displays, to touch screens.

SUMMARY

The disclosure provides for methods for the direct optical visualization of graphene and its nanoscale defects on transparent substrates. The method is useful for analyzing the manufacture of graphene devices and components for industrial applications.

The excellent IRM contrast offers a possibility to quantify local reaction progress. As IRM achieves diffraction-limited spatial resolution of ~300 nm, its signal is the local average of the contrast from graphene and graphene oxide (GO) within the diffraction limited spot, and so is linearly dependent on the local fraction of GO following the following equation.

$$C_{sample} = I_{sample}/I_0 = d_{ox} C_{GO} + (1-d_{ox}) * C_{GR}$$

Here, $I_{sample}$ and $I_0$ are the respective light intensities measured from the graphene sample and the bare substrate. $C_{GO}$ and $C_{SR}$ are the respective IRM contrast for GO and graphene under the same IRM measurement configuration. $d_{ox}$ is the oxidation degree of the measured sample. Above equation can be used to obtain the oxidation degree of graphene ($d_{ox}$) with measured IRM contrast from the sample. $C_{GR}$ and $C_{GR}$ are respectively 0.70-0.73 and 0.97 for aqueous top media.

By using IRM for imaging graphene, excellent contrast for graphene of different layers was experimentally achieved. Moreover, the imaging and provided quantitative explanation for the results.

In a particular embodiment, the disclosure provides a method for the direct optical visualization of graphene and its nanoscale defects comprising: preparing a sample comprising graphene on a transparent substrate; overlaying the sample with a liquid medium; and imaging the sample using interference reflection microscopy (IRM). In a further embodiment, the sample is prepared by transferring one or more layers of graphene to a transparent substrate using a wet-transfer process with polymethyl methacrylate (PMMA) protection. Examples of a wet-transfer process with polymethyl methacrylate (PMMA) protection comprises: spin coating a layer of PMMA onto a copper foil comprising graphene; removing the copper foil by etching to form a graphene-PMMA stack; removing traces of ferric chloride by washing the graphene-PMMA stack with water; and transferring graphene-PMMA stack to a transparent substrate. In an alternate embodiment, the sample is prepared by transferring one or more layers of graphene to a transparent substrate using a wet-transfer process without PMMA protection. Examples of a wet-transfer process without polymethyl methacrylate (PMMA) protection comprises: etching a sample comprising copper foil and graphene to remove the copper foil; stamping the etched sample with a cleaned transparent polymer substrate; and air-drying and rinsing the stamped graphene sample with water. In yet another alternate embodiment, the sample is prepared by transferring one or more layers of graphene to a transparent substrate using a dry-transfer process using thermal release tape. In yet another alternate embodiment, the sample is prepared by transferring one or more layers of graphene to a transparent substrate using a dry-transfer process using transparent adhesive tape. In a further embodiment, the liquid medium is water, isopropanol, ethanol, methanol, or an organic solvent. In a particular embodiment, the liquid medium is water. In a certain embodiment, the IRM is performed using a conventional wide-field epifluorescence microscope equipped with a standard lamp for fluorescence microscopy and an oil-immersed objective lens. In yet a further embodiment, the IRM is configured with a 50/50 beam splitter and equipped with a 530/10 nm band pass filter. In a certain embodiment, the intensity of reflected light is determined using the following equation:

$$I = |r|^2 I_l = \left| \frac{e^{i\varphi} r_{12} + e^{-i\varphi} r_{23}}{e^{i\varphi} + e^{-i\varphi} r_{12} r_{23}} \right|^2 I_l.$$

In yet a further embodiment, a method disclosed herein provides one or more of the following advantages: ultrahigh contrast for graphene layers; accurate determination of local layer numbers; ultrahigh contrast for nanoscale structures and defects; provides image contrasts >10-fold better than SEM and AFM; can be used with rough and non-conductive substrates; ultrahigh throughput that is only limited by camera frame rate; label-free and/or non-invasive; keeps the sample intact during imaging; and/or does not require vacuum or sophisticated optics. In another embodiment, a method disclosed herein provides the following advantages: ultrahigh contrast for graphene layers; accurate determination of local layer numbers; ultrahigh contrast for nanoscale structures and defects; provides image contrasts >10-fold better than SEM and AFM; can be used with rough and non-conductive substrates; ultrahigh throughput that is only limited by camera frame rate; label-free and/or non-invasive; keeps the sample intact during imaging; and does not require vacuum or sophisticated optics. In a certain embodiment, a method disclosed herein is used in one or more of the following applications: ultrahigh-throughput, ultrahigh-contrast inspection of the quality of graphene for nanoscale defects over large areas; locating and identifying graphene films or pre-patterned graphene structures during fabrication; characterization of nanoscale defects in graphene during nanofabrication processes; in situ characterization of how graphene-based flexible electronics fail under mechanical stresses; and direct visualization of how graphene-based electronics break down due to current overload or electrostatic discharge (ESD).

The disclosure also provides a method to quantify local oxidation degree of graphene with IRM contrast. IRM contrast offers a the ability to quantify local reaction progress. As IRM achieves diffraction-limited spatial resolution of ~300 nm, its signal is the local average of the contrast from graphene and graphene oxide (GO) within the diffraction limited spot, and so is linearly dependent on the local fraction of GO following the following equation:

$$C_{sample} = I_{sample}/I_0 = d_{ox}C_{GO} + (1-d_{ox})*C_{GR}$$

Here, $I_{sample}$ and $I_0$ are the respective light intensities measured from the graphene sample and the bare substrate. $C_{GO}$ and $C_{GR}$ are the respective IRM contrast for GO and graphene under the same IRM measurement configuration. $d_{ox}$ is the oxidation degree of the measured sample. Above equation can be used to obtain the oxidation degree of graphene ($d_{ox}$) with measured IRM contrast from the sample. $C_{GR}$ and $C_{GR}$ are respectively 0.70-0.73 and 0.97 for aqueous top media.

DESCRIPTION OF DRAWINGS

FIG. 11A-D provides additional IRM images of graphene on glass substrates. (A, B) Obtained using a 100× oil-immersion objective. (C, D) Obtained using a 60× water-immersion objective. FD: field diaphragm of the microscope. "0" marks areas with no graphene coverage.

FIG. 18A-D provides additional IRM images of graphene on PVC substrates. (A, B) Graphene was transferred using thermal release tapes. (C, D) Graphene was transferred using wet transfer without PMMA protection. Images were obtained using a 100× oil-immersion objective (A-C) or a 60× water-immersion objective (D). FD: field diaphragm of the microscope. "0" marks areas with no graphene coverage.

FIG. 19A-C demonstrates that SEM leads to poor contrast and noticeable structural changes for graphene on Aclar. (A) IRM image of graphene on Aclar, showing a monolayer with voids, typical wrinkles, and small islands of bilayers. (B) SEM image of the same area shows a roughened surface; voids are observed due to surface charging, but wrinkles and bilayers are not observed. (C) A subsequent SEM image of the same area taken immediately after (B), showing that significant morphological changes occurred over the entire field, attributable to instability of polymer under electron beam.

FIG. 21A-F shows IRM reveals spatially inhomogeneous oxidation of graphene. (A) Raman spectroscopy of graphene after 1 h oxidation in Clorox, taken close to (Spot A) and far away from (Spot B) centers of the flower-like patterns visualized by IRM (inset), respectively. (B,C) IRM images of graphene on glass, before (B) and after (C) 1 h oxidation in Clorox; "0" marks areas with no graphene. (D) Result of (C) converted to oxidation progress map (color-scale bar below). (E, F) Conventional transmission light microscopy of the bottom half of the same areas as (B,C), with 2× artificial enhancement of image contrast. Scale bars: 5 µm.

FIG. 22A-H shows in situ recording of the oxidation kinetics of graphene. (A) IRM image of the starting monolayer graphene; "0" marks an area with no graphene coverage. (B,C) IRM-derived oxidation progress map of the same area after 10 min (B) and 38 min (C) reaction with Clorox. (D) IRM signal (left axis) and the converted oxidation progress (right axis) as a function of time for the four pixels marked as 1-4 in (A-C, E-H). (E-H) Map of local reaction rates, obtained by calculating the slopes of reaction progress of every pixel during the time frame indicated in each figure. Arrows in (A,B,E) point to reaction-initiation centers. Scale bars: 5 µm.

DETAILED DESCRIPTION

Figure 1:
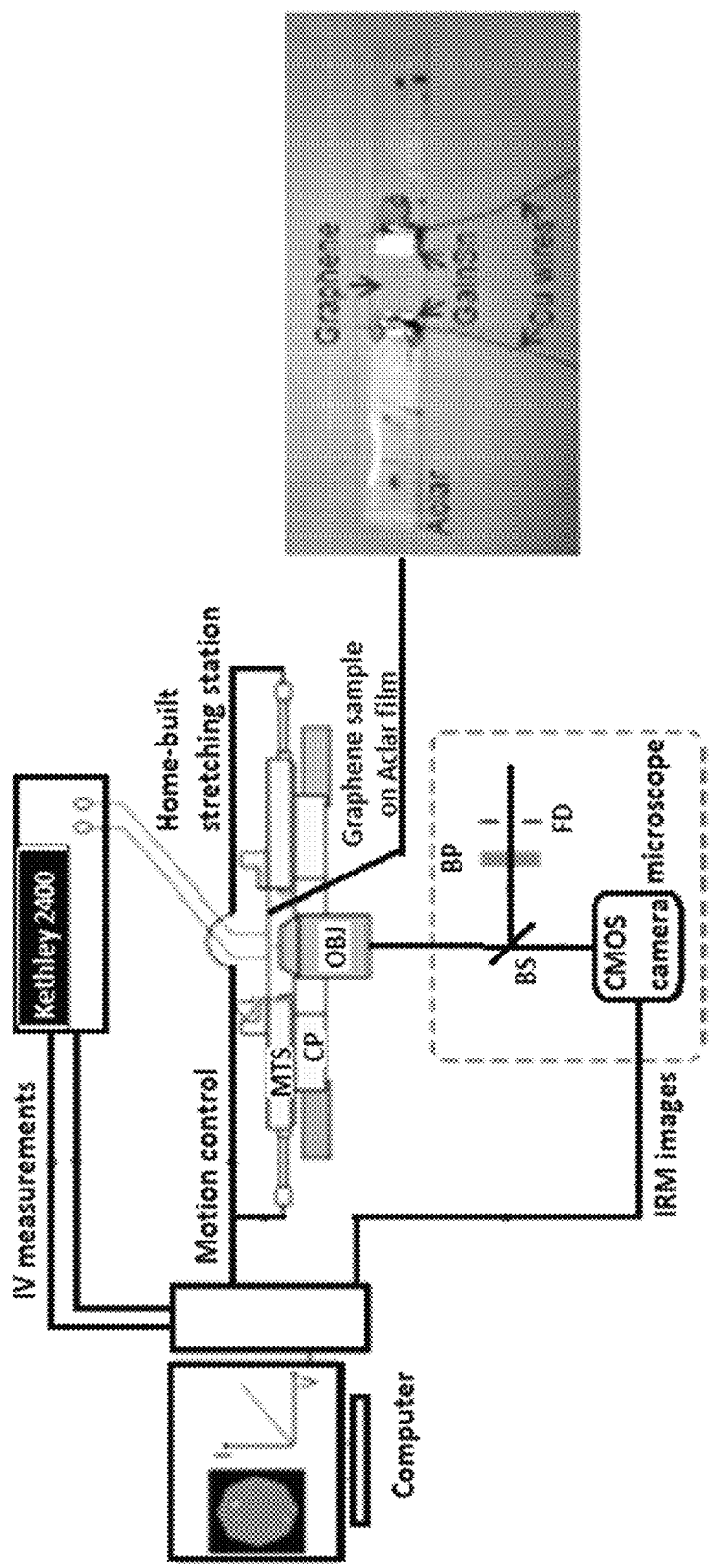
FIG. 1 presents an experimental setup for concurrent IRM and electrical characterization of graphene under stretching. CP: Central plate of the microscope. MTS: motorized translation stage. CL: clamp. Inset: photo of the sample. A GaInSn liquid metal was employed to achieve reliable contact to graphene during stretching.

As used herein and in the appended claims, the singular forms "a," "an," and "the" include plural referents unless the context clearly dictates otherwise. Thus, for example, reference to "a nanoscale defect" includes a plurality of such defects and reference to "the graphene film" includes reference to graphene films and equivalents thereof known to those skilled in the art, and so forth.

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

Also, the use of "or" means "and/or" unless stated otherwise. Similarly, "comprise," "comprises," "comprising" "include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated by reference in full for the purpose of describing and disclosing methodologies that might be used in connection with the description herein. The publications are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

The ~10% optical contrast of graphene on specialized substrates like oxide-capped silicon substrates, together with the high-throughput and noninvasive features of optical microscopy, have greatly facilitated graphene research for the past decade. However, transparent and flexible electronics, which currently stand as key commercial applications of graphene, are incompatible with these substrates. Direct optical visualization of graphene on transparent substrates remains a challenge: limited contrast is achieved, and local number of graphene layers is difficult to quantify, even with sophisticated setups. Visualization of nanoscale defects in graphene, e.g., voids, cracks, wrinkles, and multilayers, formed during either growth or subsequent transfer and fabrication steps, represents yet another level of challenge for most device substrates. Scanning electron microscopy (SEM), atomic force microscopy (AFM), and Raman spectroscopy are low in throughput, prone to sample damage, and impose stringent requirements on substrate properties. Fluorescence quenching microscopy provides a powerful optical means to visualize graphene, but a fluorescent coating is required, and nanoscale defects are still difficult to detect. Above all, it remains a challenge to characterize microscopic structures and defects in graphene on any device substrate.

It has been observed that defects during fabrication of graphene sheets can cause short circuit. Such defects include wrinkles in the graphene sheet. While not wanting to be bound by theory, the wrinkle causes a bump or defect, which causes irregular deposition of subsequent layers leading to an exaggeration in the initial wrinkle causing a short circuit. Thus, a wrinkle in the graphene sheet may be a root cause of failure of a device comprising a graphene sheet.

The term "graphene" as used herein refers to a polycyclic aromatic molecule formed of a plurality of covalently bonded carbon atoms. The covalently bonded carbon atoms may form a six-membered ring as a repeating unit, and may further include at least one of a five-membered ring or a seven-membered ring. Thus, the graphene appears as a single layer of covalently bonded carbon atoms, and each carbon atom may be $sp^2$ hybridized. A graphene sheet may comprise a single layer of graphene. Alternatively, the graphene sheet may comprise multiple layers of graphene which are stacked upon one another. A graphene sheet may have a thickness of about 0.335 nanometers (nm) to 100 nm or more.

A graphene sheet may include 1 to about 300 layers of graphene or more (e.g., 2-3, 2-4, 2-5, 5-8, 8-10, 10-20, 20-30 etc. and any integer between any of the foregoing values). However, it will be recognized that the electrical properties change as more layers are added. Accordingly, a desired layer is a layer that provides a desired electrical property of a graphene sheet.

An ideal graphene sheet has none or minimal number of defects. Ideally, a homogenous sheet of graphene will have as few defects in the sheet as possible per unit area. For example, the homogeneity of a graphene sheet may be described by the number of wrinkles per unit area of the graphene sheet. As used herein, a wrinkle in a graphene sheet refers to a ridge or furrow in the graphene sheet, as may result from contraction or folding of the graphene sheet, contraction or folding of a graphene layer of the graphene sheet, or as may result from a discontinuity in the carbon lattice structure of the graphene sheet. While not wanting to be bound by theory, it is understood that the wrinkle may be formed during formation of the graphene. The wrinkle may also be formed during the preparation of a graphene sheet, and in particular may be formed when separating or transferring the graphene sheet. Also, the wrinkle may be generated if graphene is not uniformly grown in a particular area when growing the graphene. The wrinkle is more likely to occur in a large graphene sheet. Also, a graphene sheet having fewer wrinkles provides a more homogeneous graphene sheet having better electrical characteristics.

The graphene sheet may have about 10 or fewer wrinkles, specifically about 5 or fewer wrinkles, more specifically about 3 or fewer wrinkles, per 1000 $\mu m^2$ of the graphene sheet.

A graphene sheet may have an area of a couple of square millimeters to hundreds of square meters and any value there between. Moreover, the "sheet" may be a "ribbon" that has a length dimension that is longer than a width dimension. The graphene sheet may have any shape, and is not limited to a specific shape. For example, the graphene sheet may have a circular shape, a rectangular shape, a polygonal shape, an irregular shape, or a three-dimensional shape. In this regard, the size of the graphene sheet may be determined based on lateral and longitudinal lengths measured at an appropriate location according to the shape of the graphite sheet. For example, for a graphene sheet having a circular shape, the lateral and longitudinal dimensions of the graphite sheet may correspond to a diameter of the circular graphene sheet. For a graphene sheet having an oval shape, the lateral and longitudinal dimensions of the graphite sheet may correspond to major and minor axes of the oval graphene sheet, respectively. For a graphene sheet having a polygonal shape, the lateral and longitudinal dimensions of the graphite sheet may correspond to the longest and shortest axes of the polygonal graphene sheet, respectively. The lateral and longitudinal dimensions of the graphene sheet may each independently be equal to about 1 millimeter (mm) or greater, specifically about 1 mm to about 100 meters (m), more specifically about 2 mm to about 1 m. For example, the lateral and longitudinal dimensions may each independently be about 1 mm to about 10 m, or about 1 mm to about 5 m.

A sheet as used herein can include a graphene material or functionalized form or graphene or graphene oxide. For example, a graphene sheet may comprise about 99 percent (%) or greater graphene, specifically about 99% to about 99.999% graphene, more specifically about 99.9% to about 99.99% graphene, per 1 mm$^2$ of the graphene sheet. The graphene sheet may consist essentially of, or consist of, graphene. If graphene is present in this range, the graphene sheet may be homogeneous, and thus may have uniform electrical characteristics. A graphene oxide sheet or a graphene derivative sheet can comprise 99% or greater graphene oxide or a graphene derivative. The chemical reduction of graphene oxide (GO) provides a promising route to graphene production.

A graphene sheet may be grown independently or may be grown on a substrate. The substrate may be a substrate on which graphene is directly grown or may be a substrate with a graphene sheet which has been transferred from another substrate on which the graphene was grown. The substrate and the graphene sheet may be chemically or physically directly combined with each other.

The substrate may include a metal, a non-metal, or a combination thereof to provide a stacked or layered substrate, wherein each layer of the layered substrate comprises at least one of the metal or the non-metal. The non-metal may comprise an inorganic material, and each non-metal may independently comprise, for example, silicon (Si), a glass, GaN, silica, an oxide, a nitride, or a combination comprising at least one of the foregoing.

Provided herein is a method that can directly visualize graphene on transparent inorganic and polymer substrates at 30-40% image contrast per graphene layer. As exemplified below, the non-invasive method of the disclosure overcomes typical challenges associated with transparent substrates, including insulating and rough surfaces. Moreover, the methods of the disclosure allow for unambiguous identification of local graphene layer numbers, and reveals nanoscale structures and defects with ultrahigh contrast and throughput. Further, the methods of the disclosure allow for in situ monitoring of nanoscale defects in graphene, including the generation of nano-cracks under tensile strain, at up to 4× video-rate. The disclosure also provides techniques to analyze the spatial and temporal reaction dynamics of graphene and GO.

Figure 2A:
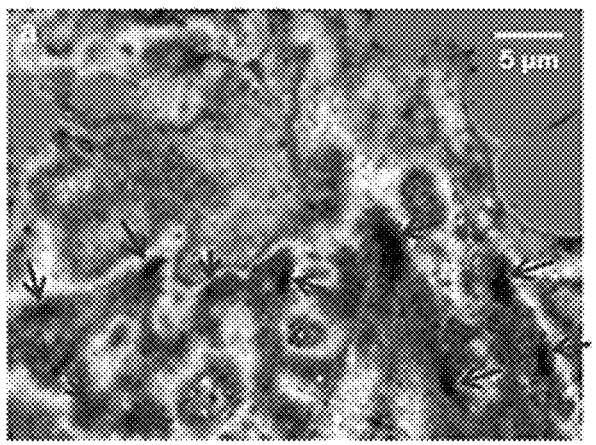
FIG. 2A-C demonstrates that in cell biology, IRM provides useful contrast for cell adhesion sites. (A) IRM image of COS-7 fibroblast cells taken under the same condition as graphene in this study. (B) Fluorescence microscopy of the phalloidin-labeled actin cytoskeleton of the same area. (C) Bright-field transmission light microscopy of the same area. Arrows in (A) point to dark areas in IRM that correspond to cell adhesion sites, which match well to focal adhesion sites at the ends of actin stress fibers as visualized in the fluorescence image (B). In comparison, no contrast for adhesion sites is observed in transmission microscopy (C).
Figure 2B:
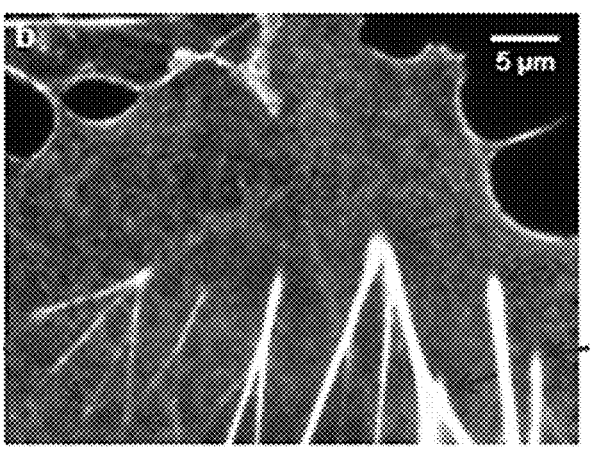
Figure 2C:
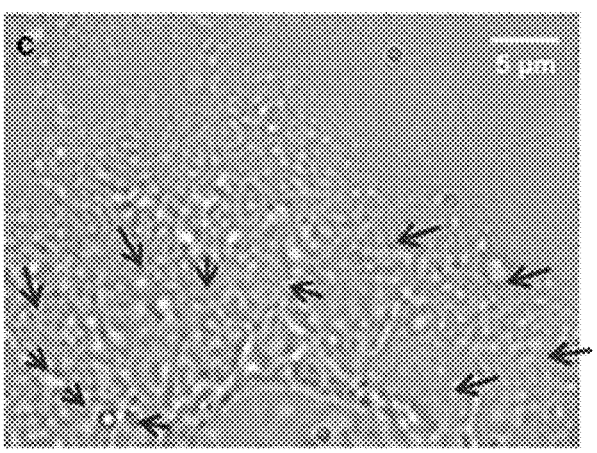
Figure 3A:
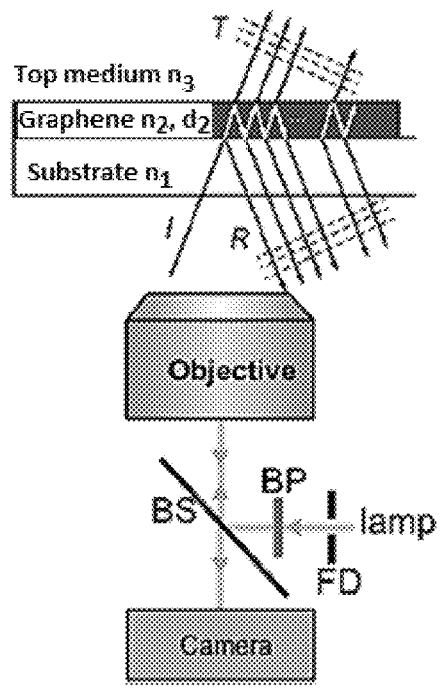
FIG. 3A-E provides for IRM visualization of graphene. (A) Schematic of setup. FD: field diaphragm; BP: band-pass filter; BS: beam splitter. (B) IRM image of graphene multilayers on a glass substrate. Numbers indicate local layer numbers. (C) The theoretical and experimental IRM signal contrast on glass for m-layer graphene vs (m−1)-layer graphene, in comparison to that of transmission light microscopy. (D) Intensity profile along line in (C), in comparison with the theoretically predicted IRM intensity (dotted lines) and experimental result from transmission microscopy. (E) The theoretical contrast I/IO (I and I/IO being the IRM signal at the ample vs. at a bare substrate, respectively) is 0.70-0.73 for the former and 0.97 for the latter.
Figure 3B:
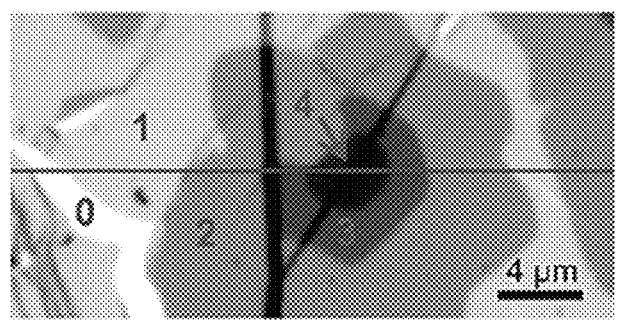
Figure 3C:
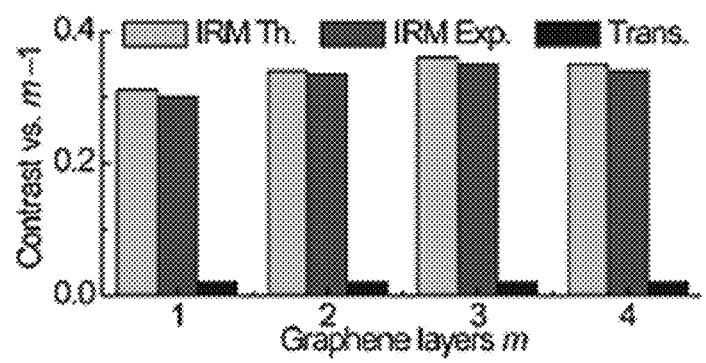
Figure 3D:
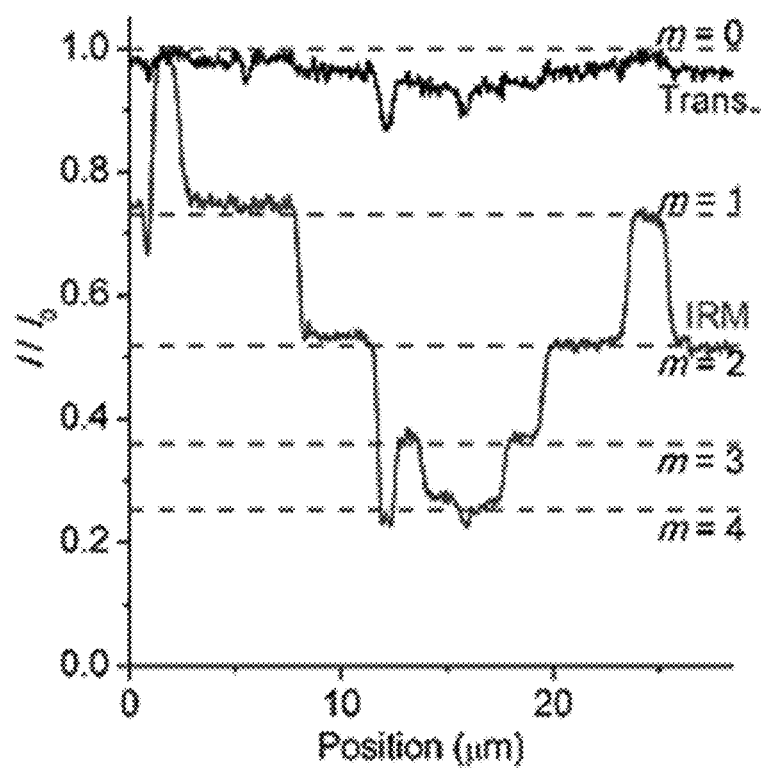
Figure 3E:
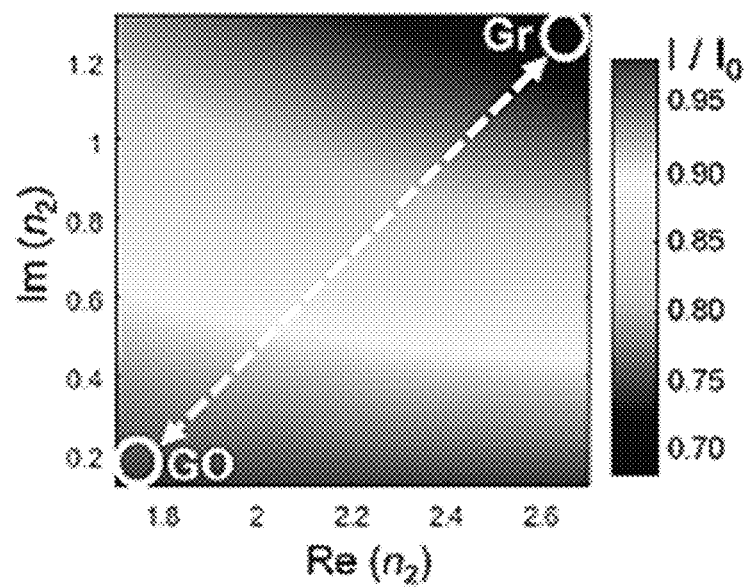

In certain embodiments disclosed herein, the disclosure provides for methods which utilize interference reflection microscopy (IRM). IRM is a facile, label-free optical microscopy method originated in cell biology. A collimated beam of filtered lamp light passes through the substrate and is reflected off interfaces between the substrate, culture medium, and cell membrane: the resultant reflection interference provides outstanding contrast for cell adhesion sites (see FIG. 2). While offering a unique means to study nanoscale cell-substrate interactions, quantitative interpretation of results has been difficult due to complex cell geometries. This technique thus previously only found very limited use in biology. IRM signal is based on the interference of light at the sample (FIG. 3A), which depends on the index of refraction of the sample, $n_2$ (FIG. 3E). As further described below, for the chemical conversion between monolayer graphene ($n_2=2.65+1.27i$) and GO ($n_2=1.75+$ 0.17i), the theoretical contrast $I/I_0$ (I and $I_0$ being the IRM signal at the ample vs. at a bare substrate, respectively) is 0.70-0.73 for the former and 0.97 for the latter (FIG. 3E) when the top medium is an aqueous solution ($n_3=1.355-1.330$).

In further embodiments disclosed herein, methods which utilize IRM can achieve excellent contrast for graphene on transparent substrates in a quantitative manner. For example, experimental optical contrast of up to 42% for monolayer graphene was achieved for transparent substrates. Moreover, the methods disclosed herein allowed for rapid and reliable detection of nanoscale graphene defects, thus enabling direct, high-throughput inspection at 4× video rate.

Figure 5A:
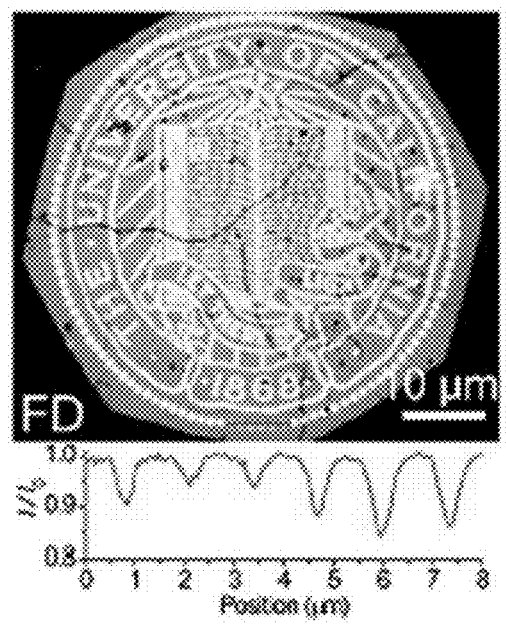
FIG. 5A-F presents IRM visualization of nanoscale structures in graphene. (A) IRM of a nano-patterned graphene monolayer on glass (top), and intensity profile along the line (bottom). FD: field diaphragm. (B) IRM of a predominantly monolayer graphene sample that was subjected to mechanical disruptions. (C) Transmitted microscopy of the same area. (D-F) IRM result (D) cross-examined with SEM (E) and AFM (F). AFM image corresponds to boxes in D, E. Insets: intensity and height profiles across the same major wrinkle that is observed in all imaging modes (vertical arrows). Arrows: bilayers; tears and fold-overs; cracks; wrinkles. Dashed arrows indicate features that are not visible in a particular imaging mode.
Figure 5B:
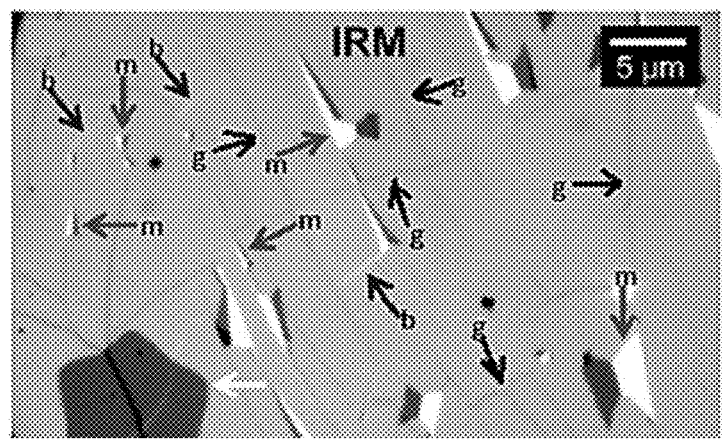
Figure 5C:
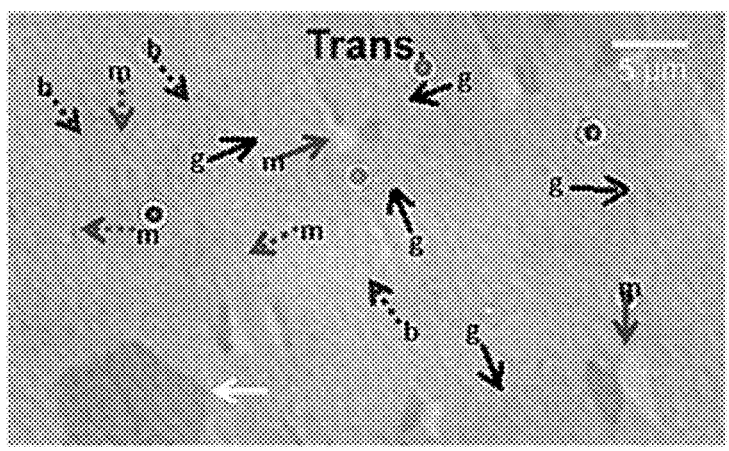

As reported herein, the methods of the disclosure provided excellent contrast for graphene grown on copper foils that was wet-transferred onto glass (see FIG. 5A), with water being the top medium. It should be noted, that the substrate can be any substrate (e.g., any transparent substrate) (see FIG. 10), and top medium can be any liquid. Intensity profiles (see FIG. 5B) were highly uniform for areas of the same m, but notably different for m=0-4. The experimental $C_m$ was 30%, 33%, 35%, and 34%, respectively, for m=1 to 4, in good agreement with predictions of Eqn. 6 (see FIG. 10C). The experimental signal-to-noise ratio for each additional layer of graphene, was found to be 34, 32, 31, and 22 for m=1 to 4, respectively. This result indicates that the methods of the disclosure allow for the unambiguous identification of graphene layers down to subpixel levels. In direct contrast, using conventional transmission light microscopy a contrast of ~2% and SNR of 2-3 were observed for each layer (see FIGS. 5B and C), illustrating the common difficulties in characterizing graphene on transparent substrates (e.g., see FIG. 5). Excellent contrast and resolution were also observed using the methods of the disclosure for a nano-patterned graphene monolayer on glass. Intensity profiles yielded ~300 nm feature widths for the finer structures, indicating that the resolution approached the diffraction limit. FIG. 5B shows a predominantly monolayer sample that was subjected to mechanical disruptions that would possibly be encountered in device fabrication. Rich features are clearly revealed, e.g., local bilayers (white arrow), tears and fold-overs ("m" arrows), and nanoscale cracks ("b" arrows) and wrinkles ("g" arrows). In comparison, in conventional transmission light microscopy (see FIG. 5C) the smaller tears are overwhelmed by noise ("m" dashed arrows) and none of the nanoscale cracks or wrinkles are discernable ("b" and "g" dashed arrows).

Figure 5D:
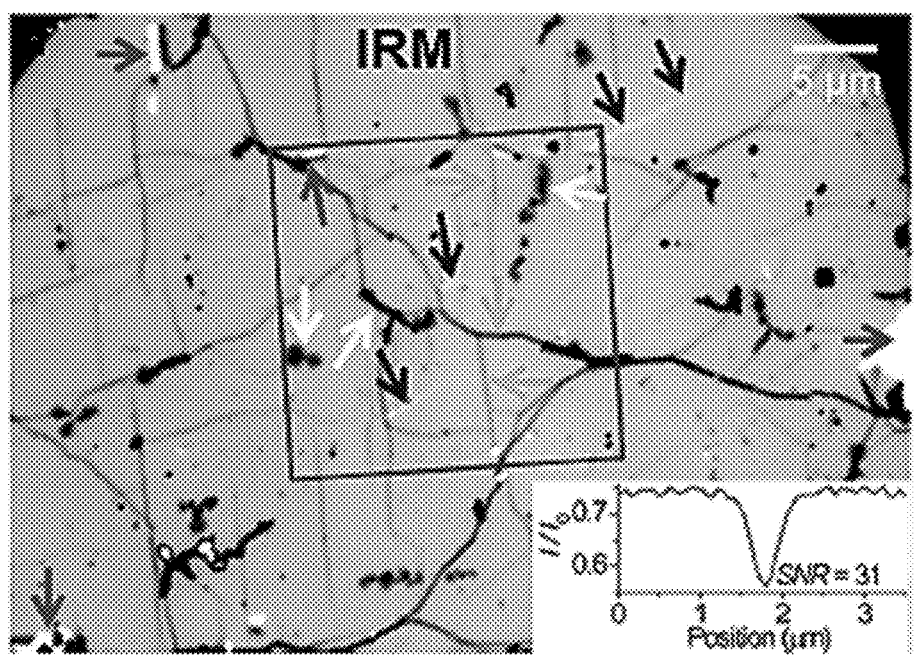
Figure 5E:
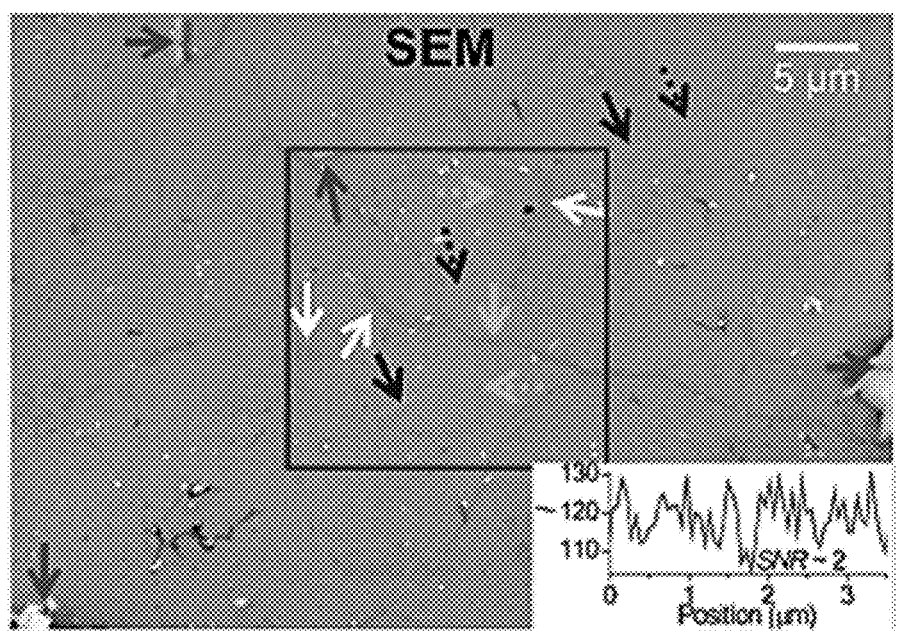

In further embodiments, the methods disclosed herein which utilize IRM provide results that were superior to those obtained using a scanning electron microscope (SEM) or an atomic force microscope (AFM) (see FIGS. 5D, E and F). For example, thinner wrinkles and cracks that are clearly resolved using IRM, are hardly observable using SEM; while using AFM, bilayers are barely visible and only the most prominent wrinkles can be detected.

Figure 9:
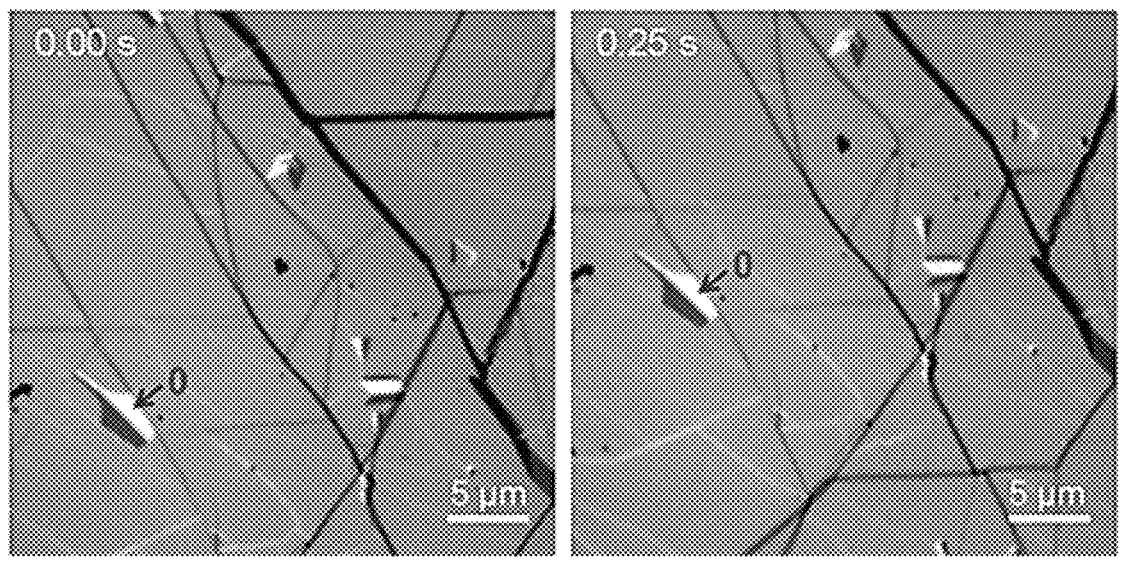
FIG. 9 provides high-throughput characterization of graphene over large areas. Video was recorded at 100 frames per second (0.01 s/frame; 4× video-rate), as the sample (graphene on glass) moved upwards. Shown here are two frames recorded at 0 and 0.25 s, respectively. Nanoscale structures and defects in graphene are clearly visualized. "0" marks an area with no graphene coverage. See also comparison with SEM and AFM results (see FIG. 5).

In other embodiments, the methods disclosed herein are further characterized by exceptional throughput, low invasiveness, and ease of operation. For example, wide-field images were captured in snapshots in ~10 ms, which is ~1,000-times and >10,000-times faster than SEM and AFM, respectively. Real-time inspection of nanoscale defects is thus readily achieved over large areas at up to 4× video-rate (see FIG. 9).

In further embodiments, the methods disclosed herein do not need to be performed in vacuo. In yet further embodiments, the methods disclosed herein are label free.

The methods of the disclosure have broad applicability to graphene on different transparent substrates (see FIG. 10). Excellent IRM contrast of 42% and 39% (see FIGS. 10A-B and H) is respectively observed for monolayers on quartz and CaF$_2$ substrates, which have been often employed for graphene physics and device applications. For flexible substrates, the methods disclosed herein achieved contrast of 23%-37% for monolayer graphene on five common polymer films, namely polychlorotrifluoroethene (Aclar), polycarbonate (PC), polyethylene terephthalate (PET), cellulose acetate (CA), and polyvinyl chloride (PVC) (see FIG. 10C-H). Nanoscale graphene structures/defects of different types were clearly visualized on all substrates using the methods of the disclosure. Moreover, it should be further noted that these characterizations are difficult to achieve with alternative techniques. Due to the very large surface roughness of commercial-grade polymer films (>10 nm), AFM often does not provide useful contrast (see FIG. 10I-J). Meanwhile, SEM provides poor contrast and causes major structural changes of the sample (see FIG. 10K-L) due to electron beam. In direct contrast, the methods of the disclosure provide nanoscale structural details for graphene on these substrates.

Additionally, the methods of the disclosure do not need to filter the light to have a certain wavelength. For example, the methods disclosed herein can utilize broadband white light. Moreover, achieving the desired contrast depends on the index of refraction rather than the nature of the top medium. Thus, the top medium can be any liquid, such as alcohols (e.g., ethanol, isopropanol, and methanol); and organic solvents.

Figure 20A:
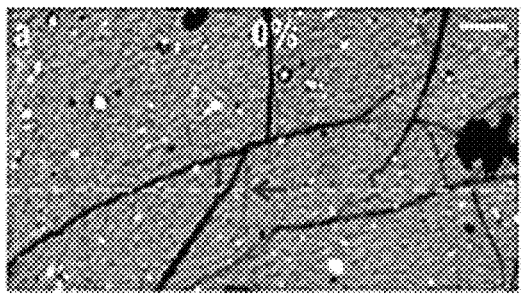
FIG. 20A-I provides in situ monitoring of the microscopic failure mode of graphene under uniaxial strain. (A-D) Four representative IRM frames recorded during stretching. Strain amount (in horizontal direction) is labeled in each image. (E) Kymograph along the lines in A-D, constructed by extracting pixels along this particular line from every IRM frame and lining them up in the vertical direction. Arrows correspond to data in (A)-(D), respectively, and point to a wrinkle that evolves into a crack during stretching. (F) Strain-dependent crack density and average crack width, determined from IRM images. (G) Concurrently measured graphene resistance. Insets: zoom-in at low strain. (H) Computer-tracked nanocracks in D with local width coded by color. Major wrinkles are drawn as white lines. (I) Kymograph of tracked cracks. Horizontal scale bars: 5 µm. Vertical scale bars: 5% strain.
Figure 20B:
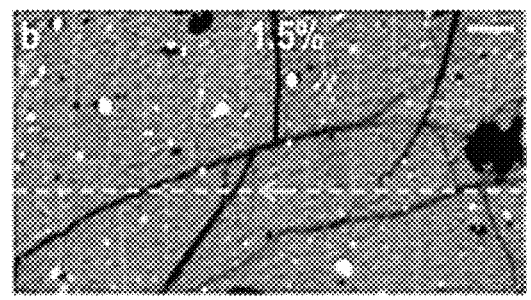
Figure 20C:
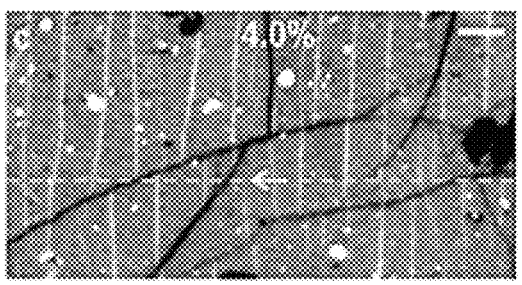
Figure 20D:
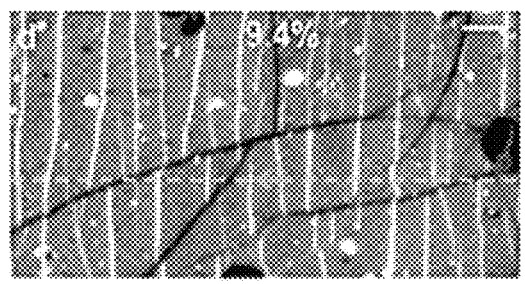

The methods disclosed herein were found to enable in situ monitoring of the microscopic failure mode of graphene under strain, an important performance parameter for flexible electronics. Frequent changes in crack orientation and position were observable using the method disclosed herein, including detecting wrinkles parallel to the stretching direction (see FIGS. 20D and H), and wrinkles perpendicular to the stretching direction (arrows in FIG. 20A-D).

The methods of the disclosure are characterized by providing one of more of the following advantages: ultrahigh contrast for graphene (30-40% or higher contrast per graphene layer); accurate determination of local layer numbers; ultrahigh contrast for nanoscale structures and defects, including voids, cracks, wrinkles, and folds, in graphene; provides image contrasts >10-fold better than SEM and AFM; can be used with rough and non-conductive substrates; ultrahigh throughput that is only limited by camera frame rate; label-free and/or non-invasive; keeps the sample intact during imaging; does not require vacuum or sophisticated optics; ease of operation and maintenance; and broadly applicable to the characterization of 2D materials.

Non-limiting examples of applications that can utilize the methods of the disclosure include, but are not limited to: ultrahigh-throughput, ultrahigh-contrast inspection of the quality of graphene for nanoscale defects over large areas; locating and identifying graphene films or pre-patterned graphene structures during fabrication to facilitate alignment between different layers, e.g., in photolithography; characterization of nanoscale defects in graphene during nanofabrication processes to understand how defects are introduced in different steps, so as to develop optimal fabrication methods; in situ characterization of how graphene-based flexible electronics fails under mechanical stresses (e.g., strain and shear), to determine the performance limit of graphene and to design more robust devices; and direct visualization of how graphene-based electronics break down due to current overload or electrostatic discharge (ESD), for guiding device design for improved performance.

The following examples are intended to illustrate but not limit the disclosure. While they are typical of those that might be used, other procedures known to those skilled in the art may alternatively be used.

EXAMPLES

Example 1

Theory. The derivations and notations follow conventions of thin-film optics. Layer configuration of the system is given in FIG. 3A. Incident light of wavelength $\lambda$ and intensity $I_I$ enters the sample from the substrate side, successively encounters graphene and top medium, and leaves as reflected (R) and transmitted (T) light. The refractive indices of the substrate, graphene, and top medium are respectively denoted as $n_1$, $n_2$, and $n_3$. Graphene thickness is $d_2$.

The Fresnel coefficients at the substrate-graphene and graphene-top medium interfaces are determined using Eqn. 1, respectively:

$$r_{12} = \frac{n_1 - n_2}{n_1 + n_2}, t_{12} = \frac{2n_1}{n_1 + n_2} \text{ and} \qquad (1)$$

$$r_{23} = \frac{n_2 - n_3}{n_2 + n_3}, t_{23} = \frac{2n_2}{n_2 + n_3}$$

The transfer matrices at the two interfaces are determined using Eqn. 2, respectively:

$$T^{12} = \frac{1}{t_{12}}\begin{bmatrix} 1 & r_{12} \\ r_{12} & 1 \end{bmatrix} \text{ and } T^{23} = \frac{1}{t_{23}}\begin{bmatrix} 1 & r_{23} \\ r_{23} & 1 \end{bmatrix} \qquad (2)$$

The transfer matrix in graphene is defined by Eqn. 3, respectively:

$$T^2 = \begin{bmatrix} e^{i\varphi} & 0 \\ 0 & e^{-i\varphi} \end{bmatrix}, \qquad (3)$$

where $\varphi = \frac{2\pi}{\lambda} n_2 d_2$

The transfer matrix for the system is defined by Eqn. 4, respectively:

$$T^{13} = T^{12} T^2 T^{23} = \frac{1}{t_{12}}\begin{bmatrix} 1 & r_{12} \\ r_{12} & 1 \end{bmatrix}\begin{bmatrix} e^{i\varphi} & 0 \\ 0 & e^{-i\varphi} \end{bmatrix}\frac{1}{t_{23}}\begin{bmatrix} 1 & r_{23} \\ r_{23} & 1 \end{bmatrix} = \qquad (4)$$

$$\frac{1}{t_{12} t_{23}}\begin{bmatrix} e^{i\varphi} + e^{-i\varphi} r_{12} r_{23} & e^{-i\varphi} r_{12} + e^{i\varphi} r_{23} \\ e^{i\varphi} r_{12} + e^{-i\varphi} r_{23} & e^{-i\varphi} + e^{i\varphi} r_{12} r_{23} \end{bmatrix}$$

The reflection coefficient is defined by Eqn. 5, respectively:

$$r = \frac{T^{13}_{21}}{T^{13}_{11}} = \frac{e^{i\varphi} r_{12} + e^{-i\varphi} r_{23}}{e^{i\varphi} + e^{-i\varphi} r_{12} r_{23}} \qquad (5)$$

Intensity of reflected light, which is recorded experimentally in IRM images is defined by Eqn. 6, respectively:

$$I = |r|^2 I_I = \left|\frac{e^{i\varphi}r_{12} + e^{-i\varphi}r_{23}}{e^{i\varphi} + e^{-i\varphi}r_{12}r_{23}}\right|^2 I_I \quad (6)$$

Meanwhile, intensity without graphene (a direct $n_1$-$n_3$ interface) is defined by Eqn. 7, respectively:

$$I_0 = \left|\frac{n_1 - n_3}{n_1 + n_3}\right|^2 I_I \quad (7)$$

It can be shown that this result is equal to that obtained through Eqn. 6 for $d_2=0$ (number of graphene layer, m=0).

Preparation of Graphene on Different Substrates a. Wet Transfer with PMMA Protection:

Graphene on glass, quartz, $CaF_2$ and Aclar (polychlorotrifluoroethene) substrates were prepared through the standard wet-transfer method with PMMA protection. CVD graphene on copper foils (Graphene Supermarket, Calverton, N.Y.) was spin-coated with a ~150 nm layer of polymethyl methacrylate (PMMA 495 A4, MicroChem, Newton, Mass.). After the copper was removed in an etching solution (5% HCl+20% FeCl3), the graphene-PMMA stack was transferred to a fresh water bath so it floated on the water surface. Water bath transfer was repeated three times to remove traces of ferric chloride. The PMMA-protected graphene film was then transferred to the target substrates. PMMA was removed in two steps using anisole (15 min) and acetone (1-2 hours) followed by a rinse of isopropanol (10 min), and the sample was dried with nitrogen gas.

b. Wet Transfer without PMMA Protection:

CVD graphene on copper was floated on top of an etching solution for 5-10 minutes to remove copper. As soon as the copper layer became invisible, a cleaned polymer substrate was used to carefully stamp the graphene piece from the top. The polymer substrate with graphene was air-dried for ~20 minutes and then rinsed with DI water.

c. Dry Transfer Using Thermal Release Tape:

Graphene transfer tape (Graphene Supermarket, GTT-5pk) was applied to a piece of CVD graphene on copper and pressed thoroughly. Copper was removed in an etching solution for ~10 minutes. Tape with graphene was rinsed in fresh DI water for three times and then briefly air-dried. The tape was applied to the polymer substrate, pressed and scraped thoroughly. A hotplate was used to heat the sample to ~90° C. for release of the tape.

d. Dry Transfer with 3M Scotch Tape:

3M Scotch 105 Magic Tape was applied to a piece of CVD graphene on copper and pressed and scraped thoroughly. Copper was removed in an etching solution for ~10 minutes. Sample was rinsed with fresh DI water for three times. After brief air-drying, the tape with graphene was applied on a cleaned polymer substrate, pressed and scraped thoroughly. The tape was gently taken off from the polymer substrate.

e. Nano-Patterning of Graphene:

Defined nano-patterns of graphene (see FIG. 5A) were fabricated using focused ion beam (FIB). A gallium ion beam in a FEI Quanta SEM/FIB system was used to pattern CVD graphene on a copper foil, and the patterned graphene was transferred to a glass substrate using PMMA-protected wet transfer as described above. Mechanically disrupted graphene samples (see FIG. 5B-C) were produced by immersing the samples in acetone and using a pipette to generate air bubbles at the graphene surface, a process that emulates what is often encountered in the lift-off process of photolithography for device nanofabrication.

Interference Reflection Microscopy (IRM).

Figure 4A:
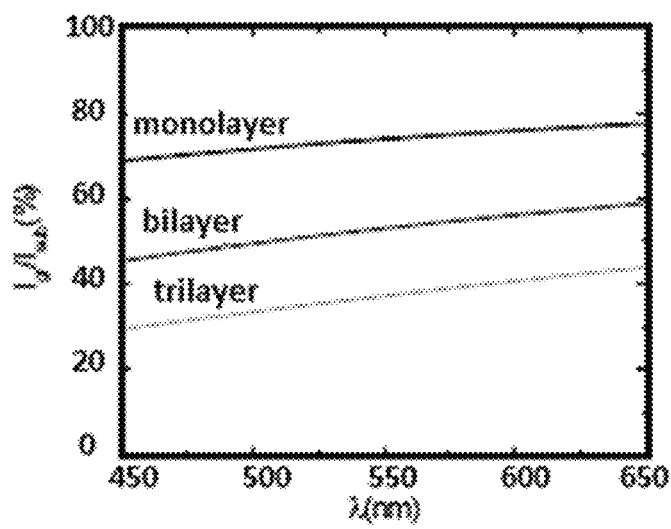
FIG. 4A-C shows that IRM contrast of graphene is relatively insensitive to wavelength. (A) Theoretical IRM signal contrast (normalized by signal intensity on bare substrate without graphene) for graphene of different layers on glass, as a function of wavelength according to Eqn. 1. (B) Experimental result with the 530/10 nm band pass filter (condition for all results presented in this work). "0" marks an area with no graphene coverage. (C) Experimental result for the same sample without the use of any optical filters: here the recorded signal is the weighted average of all wavelengths in the spectrum of the lamp convolved with the wavelength-dependent sensitivity of the camera. In the setup presented herein, the resultant contrast (30% for monolayer graphene) happens to be comparable to that when a 532/10 nm bandpass filter is used.
Figure 4B:
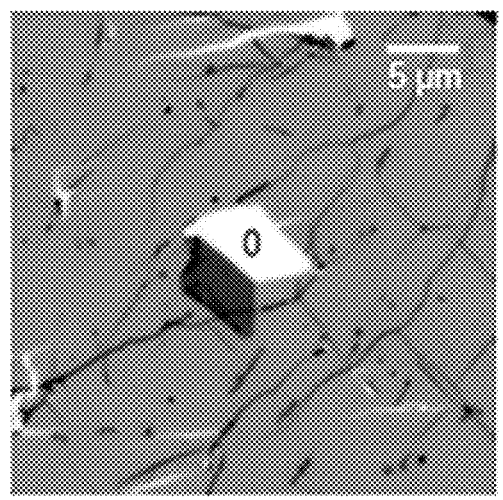
Figure 4C:
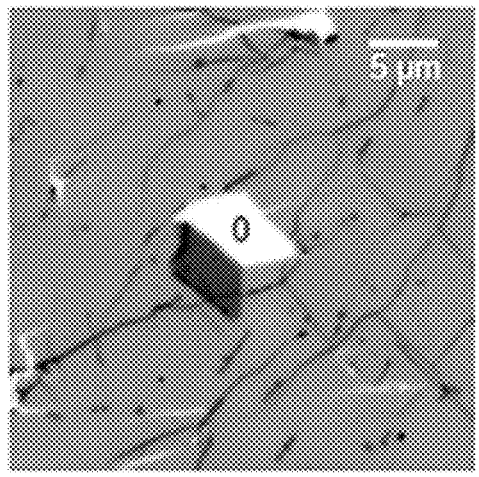

IRM was performed on a conventional Olympus IX73 inverted wide-field epifluorescence microscope that was equipped with a standard lamp for fluorescence microscopy (U-HGLGPS). The fluorescence filter cube was configured with a 50/50 beam splitter (Chroma 21000) and a 530/10 nm band pass filter (Chroma D532/10×) as the excitation filter. While the use of a band pass filter facilitated comparison of results with theory, the obtained contrast was relatively insensitive to the wavelength, and comparable contrast may be obtained without using an optical filter (see FIG. 4). No emission filter was used. Objective lenses were an Olympus UplanFl 100× oil-immersion objective (NA ~0.9 with iris diaphragm) and an Olympus UplanSapo 60× water-immersion objective (NA 1.2). Significantly reduced contrast was observed when dry objective lens was employed due to back-reflections at air-glass interfaces (~8% for monolayer graphene on glass when using an UplanSapo 20× objective), and so is not recommended. IRM images were acquired at 16-bit bit-depth using an Andor Zyla 4.2 sCMOS camera at 1024×1024 pixels with ~20 ms integration time (~50 frames per second) or at 512×512 pixels to achieve a 10 ms integration time (100 frames per second or 4× video-rate). Effective pixel size, $l_{pixel}$, was 65 nm and 108 nm when using the 100× and 60× objectives, respectively. The microscope field diaphragm was closed down to slightly smaller than the 1024×1024 frame size to reject stray light from oblique angles, hence the black edges in images. Comparable results were obtained when the entire sample was immersed in water, or when a droplet of water was deposited at the area of observation. Eqn. 6 predicts that the final results only depend on the index of refraction, rather than the nature, of the top medium. The results presented herein focused on water as it is most accessible and uniquely compatible with all the substrates used in this disclosure.

SEM and AFM Characterizations.

Figure 6A:
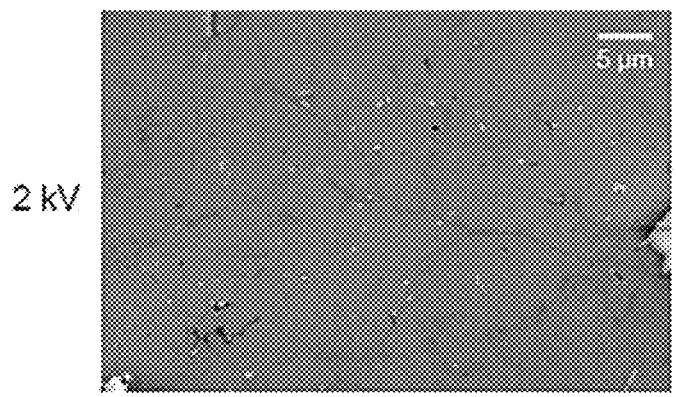
FIG. 6A-C provides a SEM of graphene on glass at different accelerate voltages (V0). (A) V0=2 kV, corresponding to FIG. 2e: this provides the best contrast. (B) V0=3 kV: Stronger charging effect is observed at the exposed glass surface, and lower contrast is observed for wrinkles. (C) $V_0$=1.5 kV: Surface charging is reduced, but image contrast and resolution both dropped. Taken together, these results illustrate the difficulties of using SEM to characterize graphene on the fully insulating glass substrate.
Figure 6B:
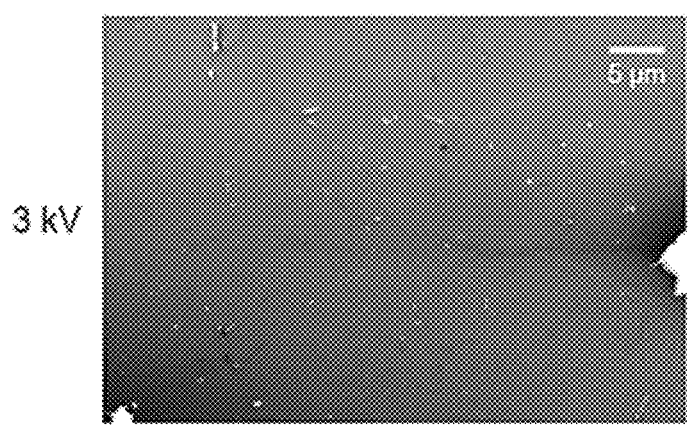
Figure 6C:
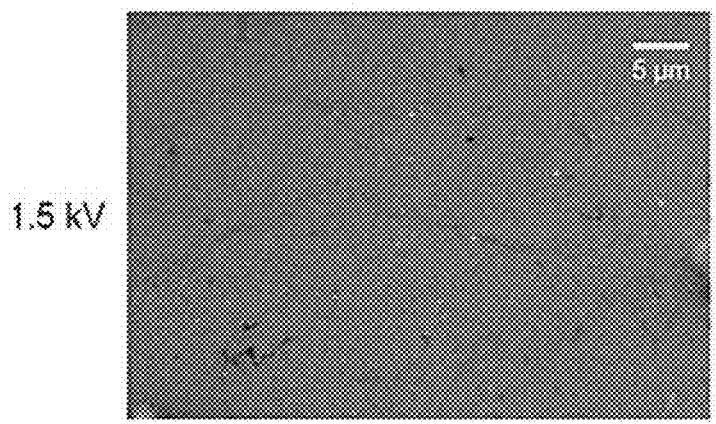
Figure 7A:
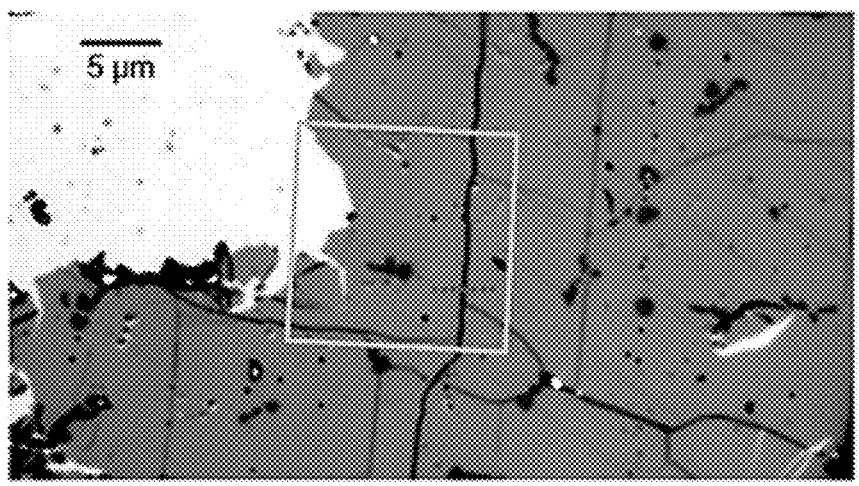
FIG. 7A-D provides additional correlated results of IRM (A), SEM (B), and AFM (C). AFM image in (C) corresponds to orange boxes in (A, B). (D) Intensity and height profiles across the same major wrinkle, corresponding to the dotted lines in the three imaging modes.
Figure 7B:
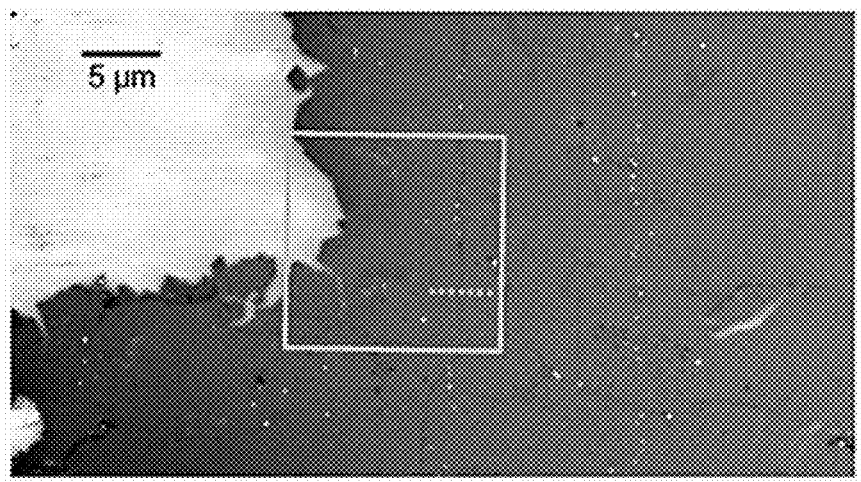
Figure 7C:
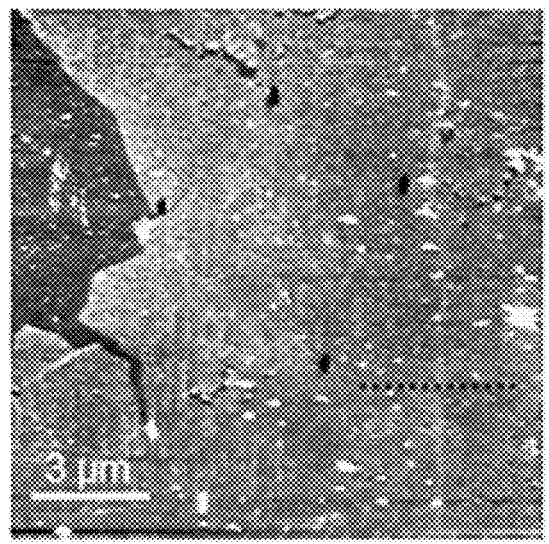
Figure 7D:
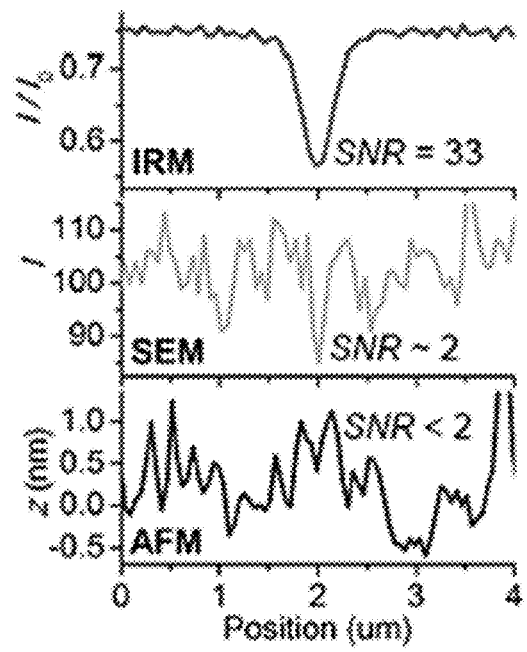
Figure 8A:
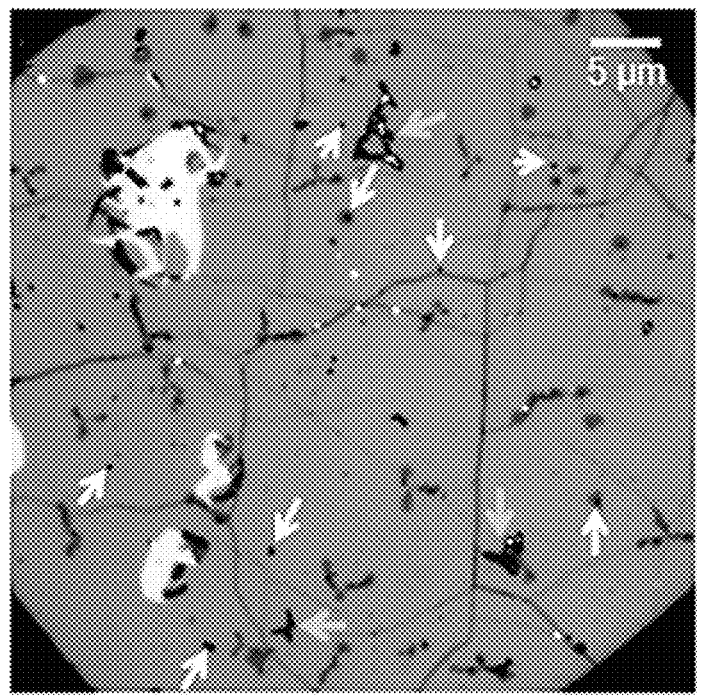
FIG. 8A-C presents visualization of nanoscale contaminants. (A-C) Correlated results of IRM (A), SEM (B), and AFM (C) images of graphene on glass. White arrows point to speckle-like debris. Other arrows point to thread-like contaminants likely due to polymer residuals from the wet-transfer process.
Figure 8B:
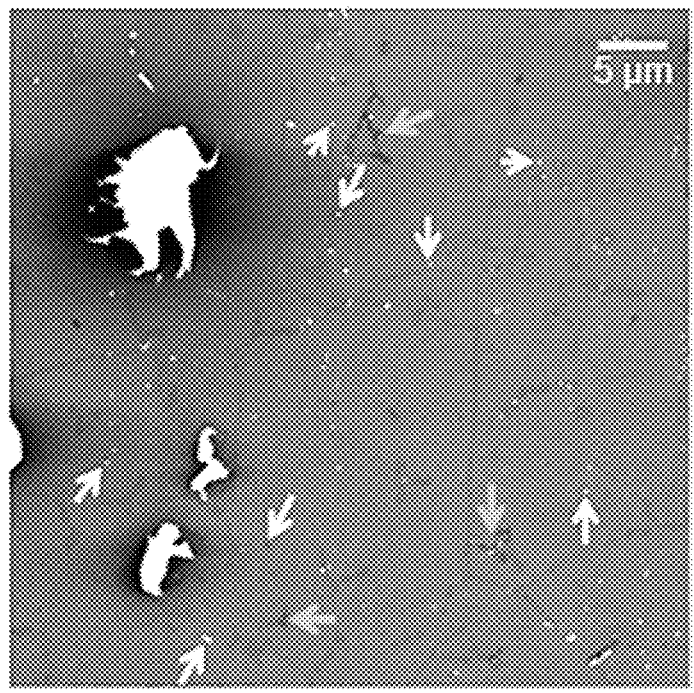
Figure 8C:
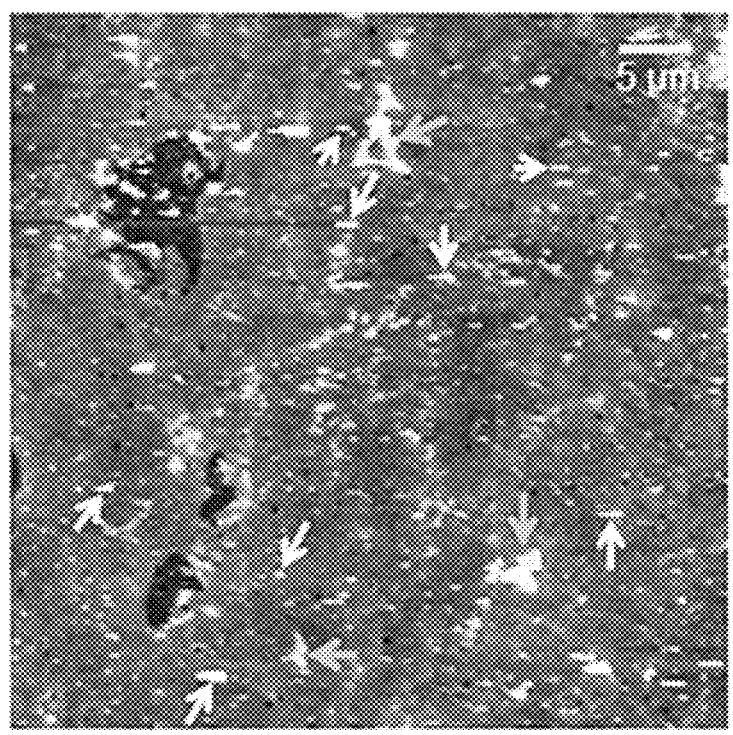

The conductivity of graphene itself was utilized to enable SEM characterization of graphene on the insulating substrates. The sample was mounted on a standard metallic sample mount using carbon tape, and a small amount of silver colloid paint (Ted Pella 16031) was used to create a conductive bridge between graphene and the sample mount. SEM imaging was performed on a FEI Quanta 3D FEG system in secondary-electron mode. Comparison of images obtained at different acceleration voltages indicated that best contrast was obtained at 2 kV (see FIG. 6), which was selected for comparison with IRM results.

AFM images were taken on an Asylum MFP-3D system in tapping mode using aluminum-coated probes (Tap150A1-G; BudgetSensors). Nominal values of the force constant, resonance frequency, and tip radius were 5 N/m, 150 kHz, and <10 nm, respectively. AFM data were processed using WsXM.

Concurrent IRM and Electrical Characterization of Graphene Subject to Uniaxial Stretching.

a. Sample Preparation:

For stretching experiments, CVD graphene (10×4 mm) was deposited at the center of a ~60×6 mm strip of a 0.2 mm-thick Aclar 33C film (Ted Pella, Redding, Calif.). A liquid metal, GaInSn (68.5%:21.5%:10%), was employed as contact electrodes to ensure reliable contact to graphene during stretching (see FIG. 1 inset). Two thin copper wires were first connected to graphene using silver paint and glued down onto the substrate with epoxy. GaInSn liquid metal was then applied to connect the graphene surface with the copper wires; final distance between electrodes was ~8 mm. The liquid metal wetted the graphene surface well and so maintained highly stable junction conductance during stretching. A control sample in which GaInSn liquid metal directly bridged two copper wires on the Aclar substrate showed a highly stable resistance of 1.36-1.38Ω during a similar stretching process, which is more than three orders of magnitude smaller than the measured resistance of graphene.

b. Measurement System:

The measurement system (FIG. 1) was comprised of three sub units, namely a homebuilt tensile-testing station to apply uniaxial strain, IRM to monitor in situ structural changes in graphene under strain, and a Keithley 2400 SourceMeter to concurrently monitor the electrical properties of graphene. The tensile-testing station was constructed by mounting two single-axis motorized translation stages (PT1-Z8, Thorlabs) onto the central plate of the microscope stage, face to face with a 50 mm gap at zero displacement. The strip-shaped sample was clamped at the two ends to the two stages so that its long axis is aligned with the translational axes of both stages. A computer program was developed to simultaneously displace the two motorized stages to opposite directions at the same rate. The system is effective for stretching graphene up to a strain of ~9.5%, when the Aclar film starts to yield. Strain was measured by examining the actual displacements of structural features within the sample from the obtained IRM images.

IRM system was as described above, but with the addition of an extension tube for the objective lens to account for the increase in height due to the stretching stages. To calculate the width of nano-cracks in monolayer graphene, which are often smaller than the diffraction-limited resolution of optical microscopy (~300 nm), the measurements were by pixel, across the crack, the intensity difference when compared to continuous graphene, $\Sigma \Delta I_{crack}$. The crack width was then determined by $w=I_{pixel}\Sigma \Delta I_{crack}/(I_0/I_1)$. Here $I_{pixel}$ is the effective pixel size, and $I_0$ and $I_1$ are the experimentally measured light intensity per pixel on blank substrate and on continuous monolayer graphene, respectively. Crack density is calculated as the number of nano-cracks per unit length in the stretching direction, averaged across the image.

A Keithley 2400 SourceMeter was used to monitor the electrical properties of graphene during stretching. Current through graphene was recorded as the voltage was continuously swept in loops between −12 mV and 12 mV. Resistance was determined by fitting to the resultant, highly linear I-V data.

Results.

A standard inverted fluorescence microscope with oil- and water immersion objective lenses was configured with a 50/50 beam splitter and a 532/10 nm bandpass filter (FIG. 1a). The f1 field diaphragm was closed down to slightly smaller than the recording frame size to reject stray light. Copper-grown graphene that was wet-transferred onto glass, with water being the top medium (see FIG. 3B) was first examined. Highly uniform IRM signal was observed for areas of the same number of graphene layers (m), while excellent contrast were observed for m=0-4 (see FIG. 3C-D). The signal contrast of each added layer, as defined by $C_m=(I_{m-1}/I_m)/[(I_{m-1}+I_m)/2]$, where $I_m$ is IRM signal intensity on m-layer graphene ($I_0$ for no graphene coverage), was 30%, 33%, 35%, and 34%, respectively, for m=1 to 4 (see FIGS. 3C and D). These results are >10-fold higher than relying on light absorption (□2&) and even 3-fold higher than that is experimentally achieved on optimized $SiO_2$-capped-Si substrates (□10%). The experimental signal-to-noise ratio for each additional layer of graphene, defined as $SNR_m=(I_m-1-I_m)/[(\sigma_{m-1}+\sigma_m)/2]$, where $\sigma_m$ is the standard deviation of signal between pixels for the same m, is found to be 34, 32, 31, and 22 for m=1-4, respectively. This result suggests that the data should enable unambiguous identification of graphene layers down to subpixel levels. In comparison, conventional transmission light microscopy, performed on the same microscope using the same objective lens (thus the same magnification and numerical aperture) and with comparable light intensities at the same camera, achieved low contrast of ~2% and SNR of 2-3 for each layer (see FIG. 3C-D), thus illustrating the common difficulties in characterizing graphene on transparent substrates.

Figure 10A:
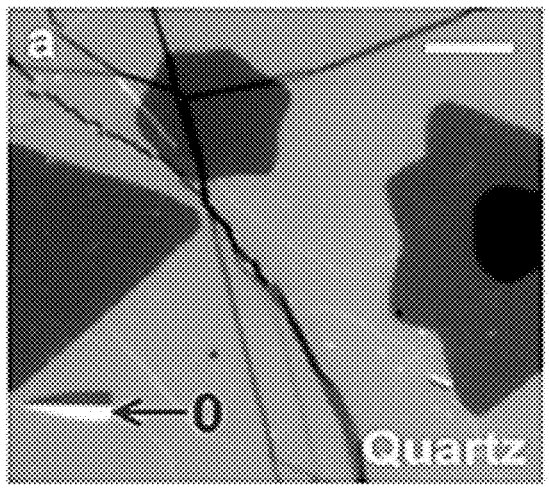
FIG. 10A-L presents IRM visualization of graphene on different transparent substrates. (A) Quartz. (B) Calcium fluoride. (C) Aclar (polychlorotrifluoroethene). (D) Polycarbonate. (E) Polyethylene terephthalate. (F) Cellulose acetate. (G) Polyvinyl chloride. (H) Measured IRM contrast for monolayer graphene on different substrates. Line: contrast of transmission microscopy. (I) AFM image of graphene on Aclar (same sample as c). (J) Height profile along the dotted line. (K) SEM image of the same sample (box in C). Dotted arrows point to where wrinkles are visualized in IRM (C). A subsequent SEM image: arrowheads point to structural changes. Scale bars: 5 μm (A-G, K, and L); 2 μm (I). "0" marks areas with no graphene coverage.
Figure 10B:
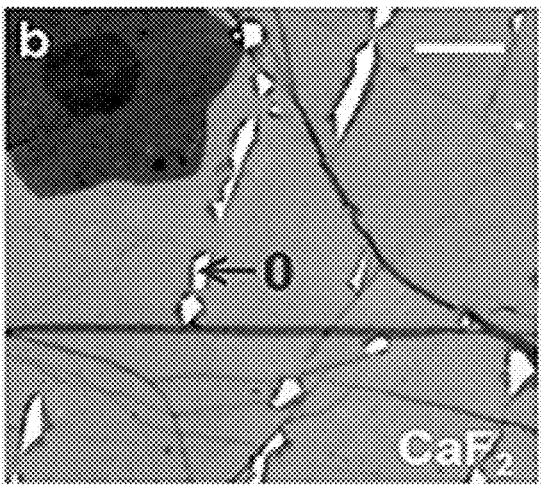
Figure 10C:
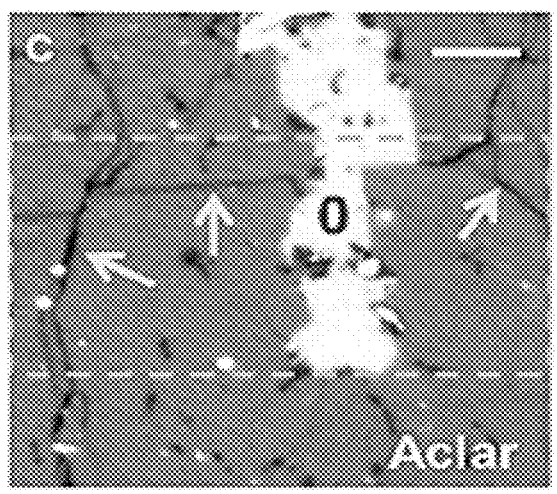
Figure 10D:
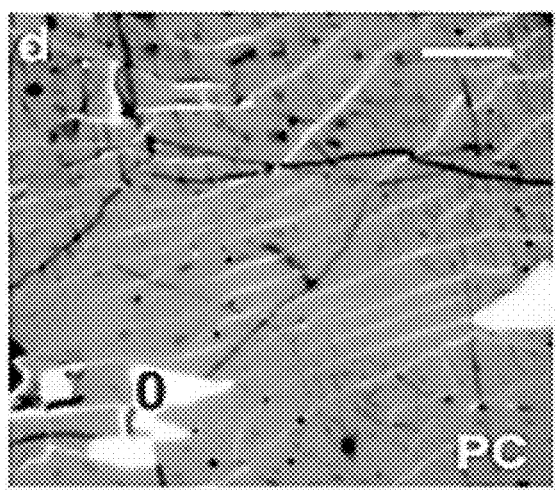
Figure 10E:
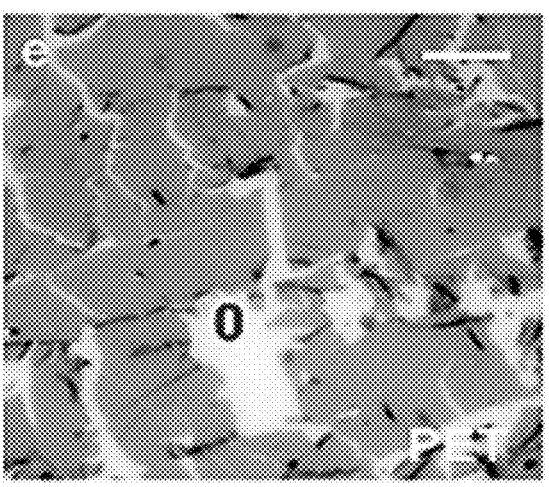
Figure 10F:
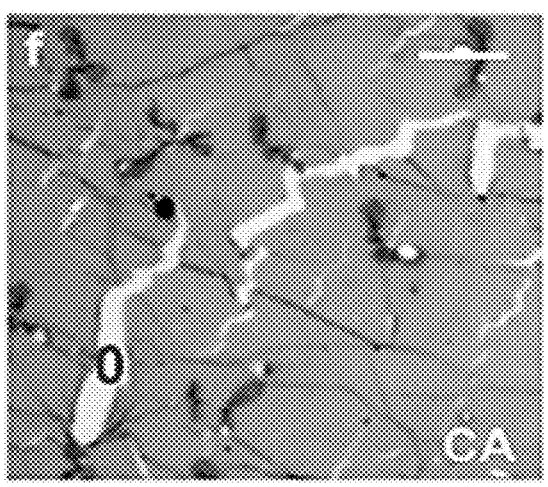
Figure 10G:
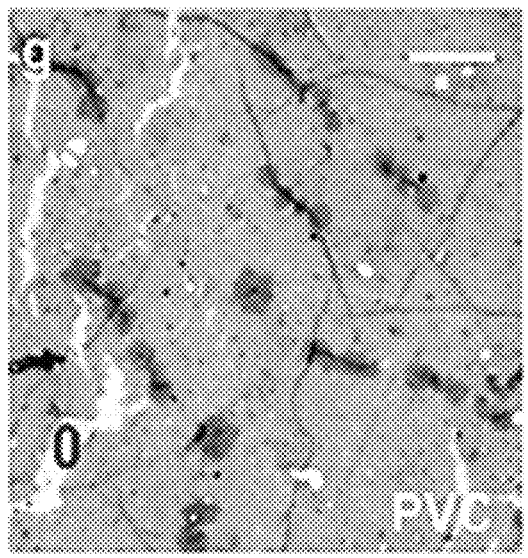
Figure 10H:
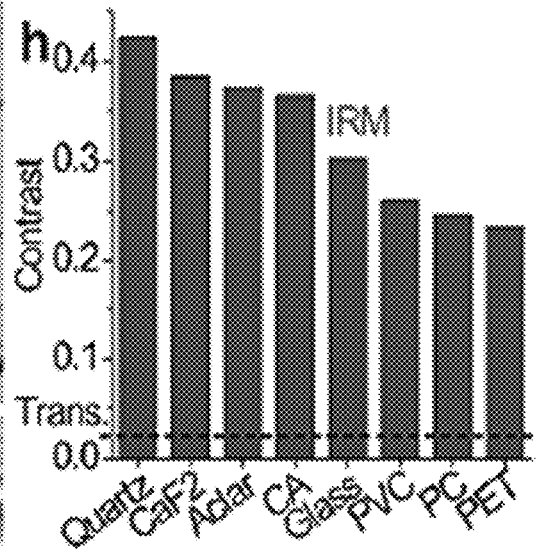
Figure 10I:
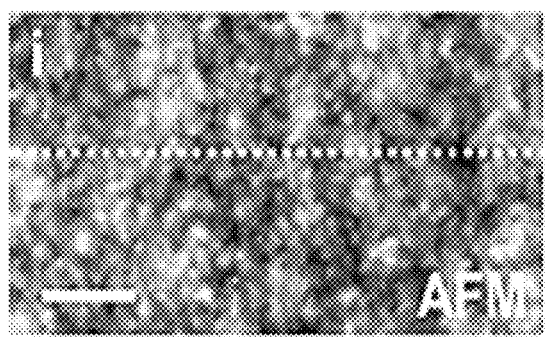
Figure 10J:
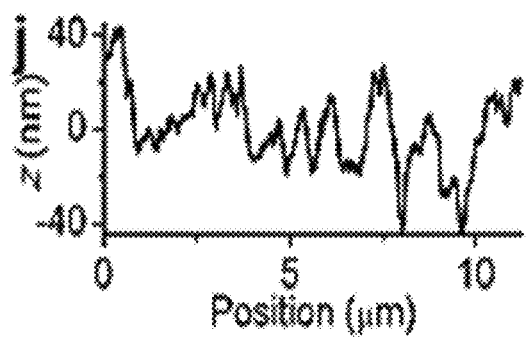
Figure 10K:
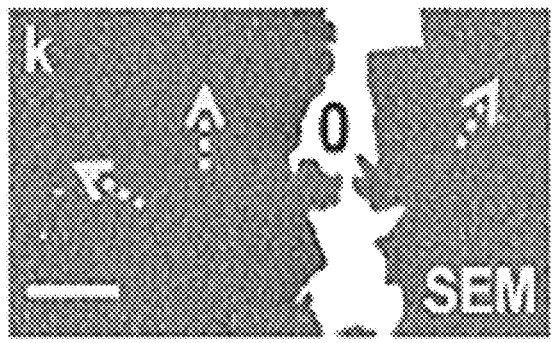
Figure 10L:
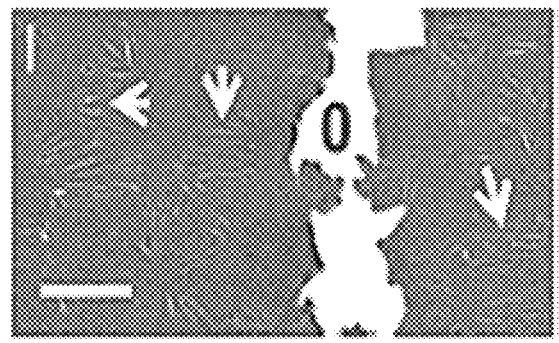
Figure 12A:
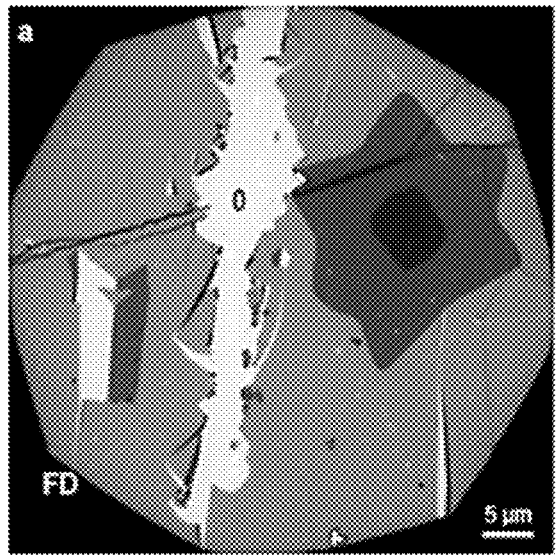
FIG. 12A-D provides additional IRM images of graphene on quartz substrates. (A-C) Obtained using a 100× oil-immersion objective. (D) Obtained using a 60× water-immersion objective. FD: field diaphragm of the microscope. "0" marks areas with no graphene coverage.
Figure 12B:
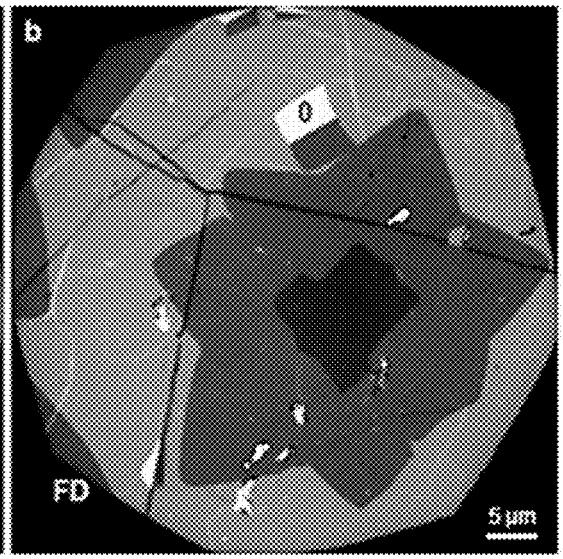
Figure 12C:
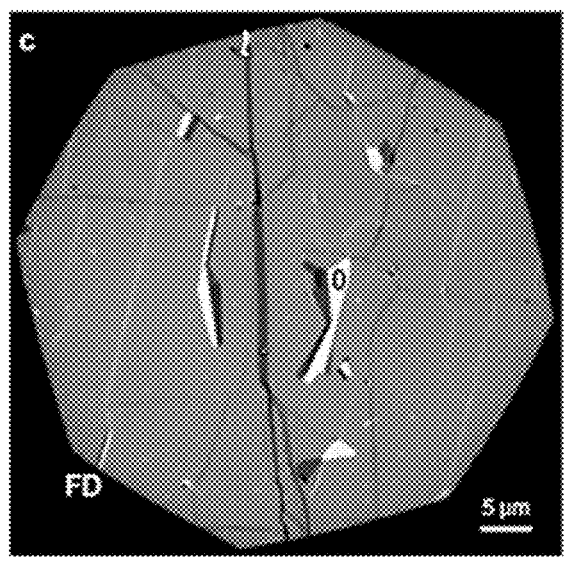
Figure 12D:
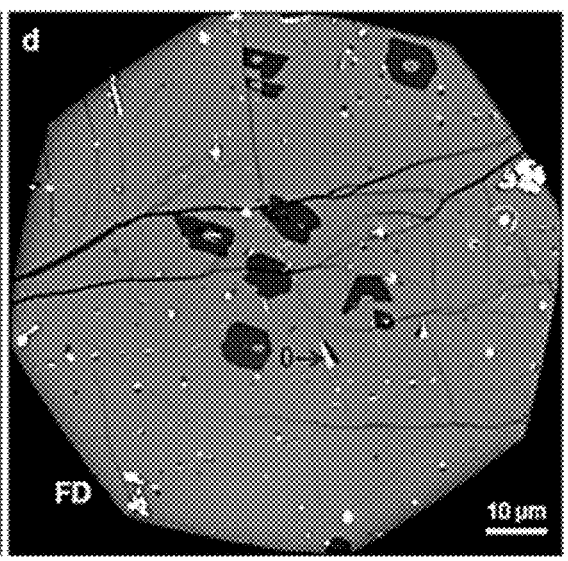
Figure 13:
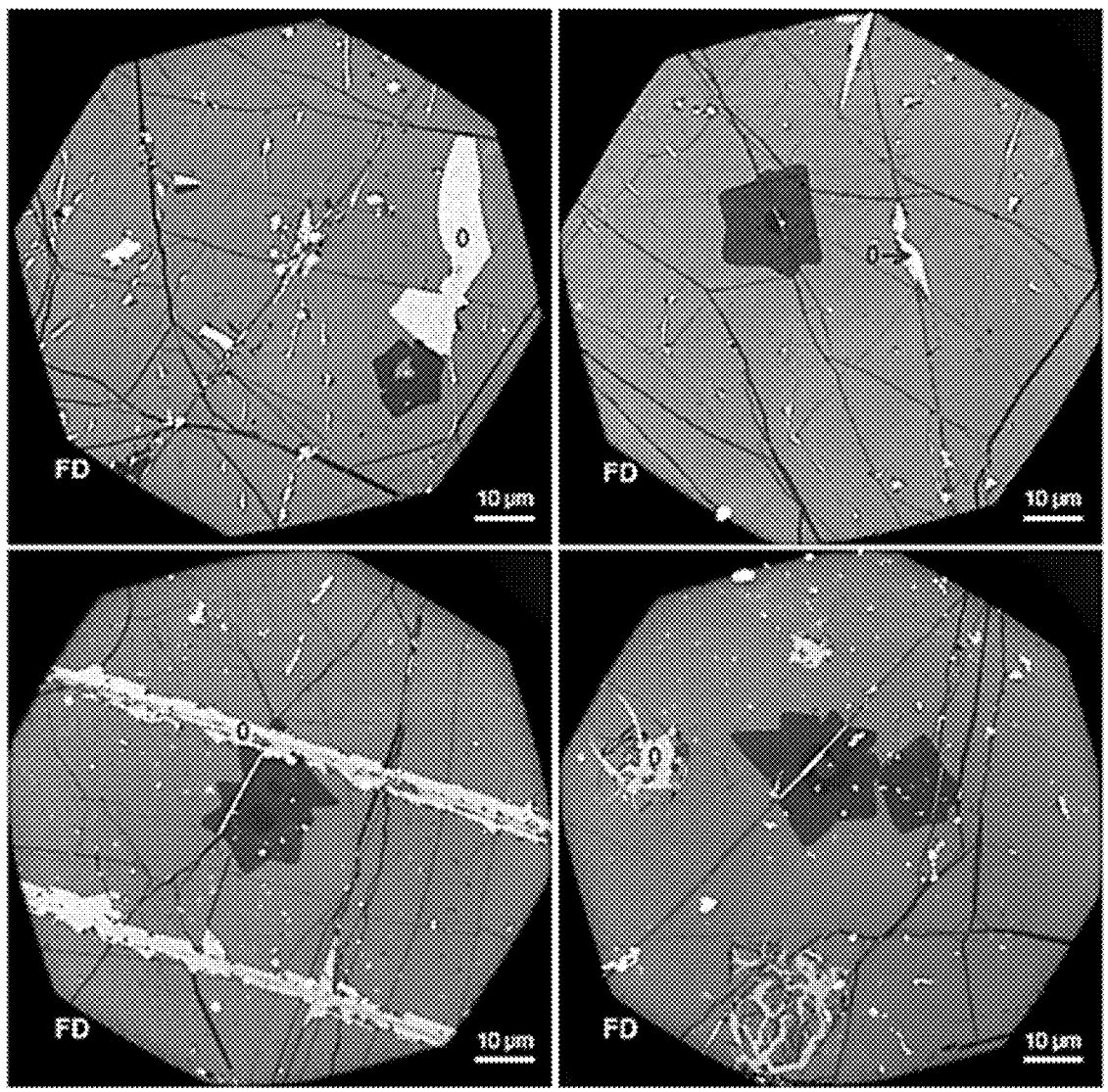
FIG. 13 provides additional IRM images of graphene on CaF2 substrates. Images were obtained using a 60× water-immersion objective. FD: field diaphragm of the microscope. "0" marks areas with no graphene coverage.
Figure 14A:
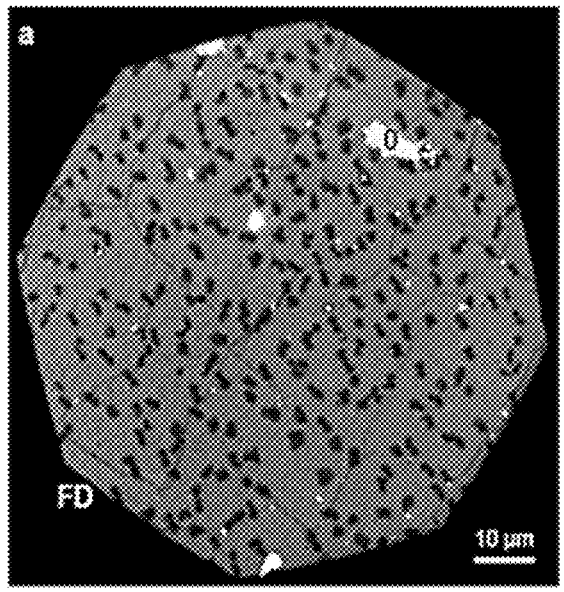
FIG. 14A-D provides additional IRM images of graphene on Aclar substrates. (A, B) Graphene transferred using standard PMMA-protected wet-transfer. (C, D) Graphene transferred using thermal release tapes. Imaged were obtained using a 60× water-immersion objective. FD: field diaphragm of the microscope. "0" marks areas with no graphene coverage.
Figure 14B:
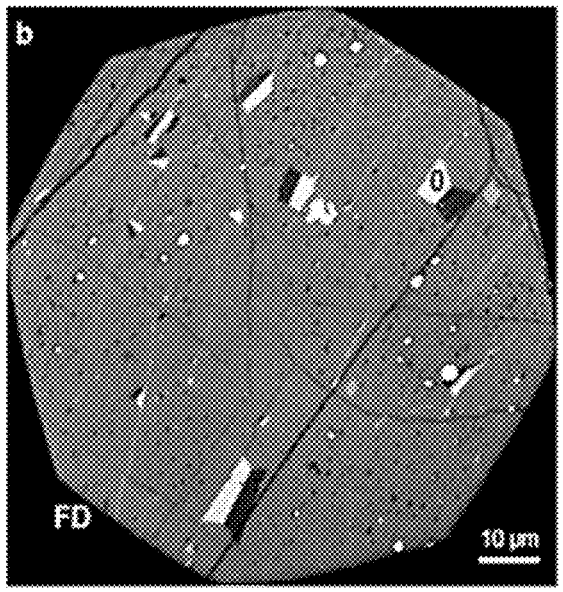
Figure 14C:
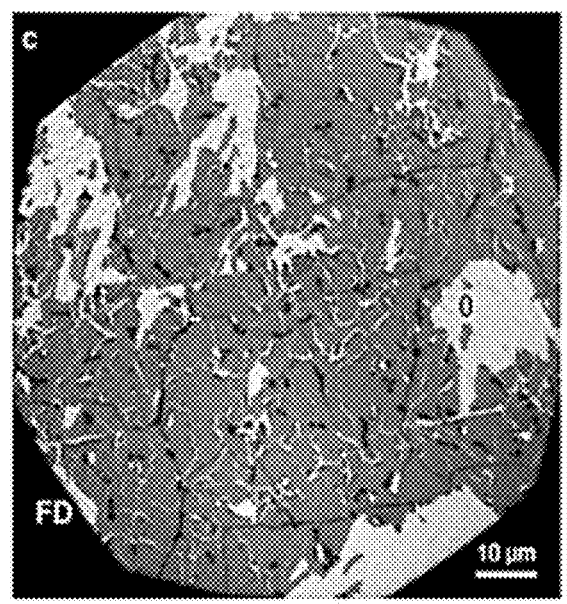
Figure 14D:
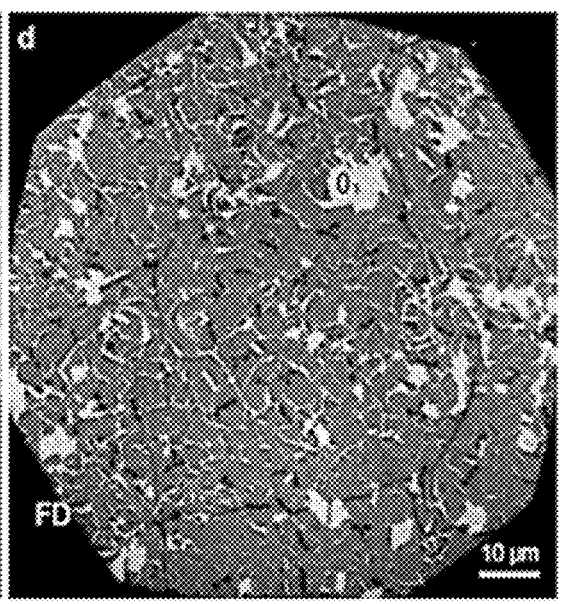
Figure 15A:
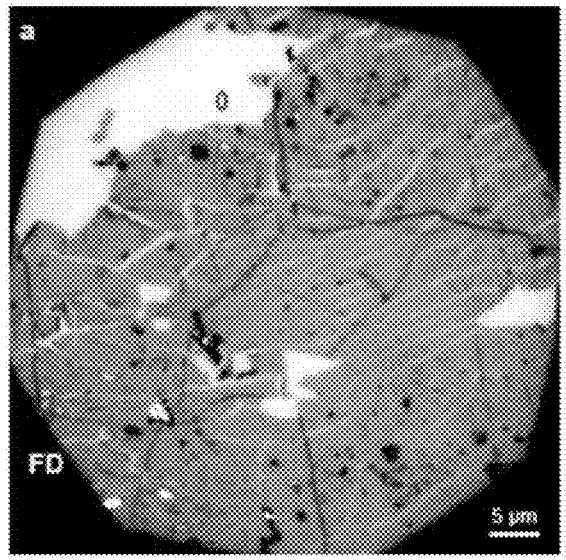
FIG. 15A-D provides additional IRM images of graphene on polycarbonate substrates. (A-C) Obtained using a 100× oil-immersion objective. (D) Obtained using a 60× water-immersion objective. Graphene was transferred using thermal release tapes. FD: field diaphragm of the microscope. "0" marks areas with no graphene coverage.
Figure 15B:
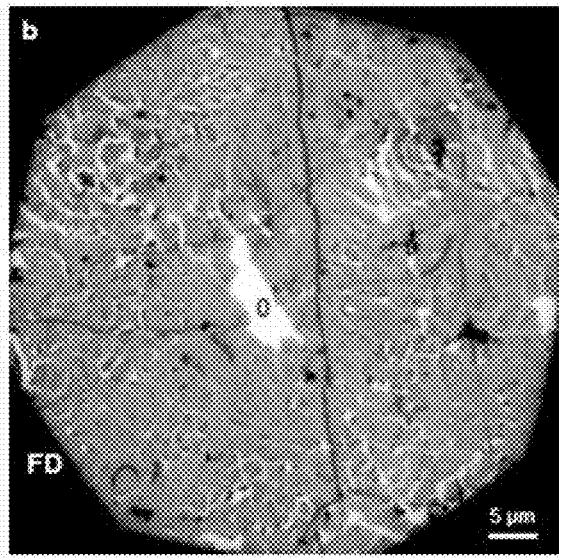
Figure 15C:
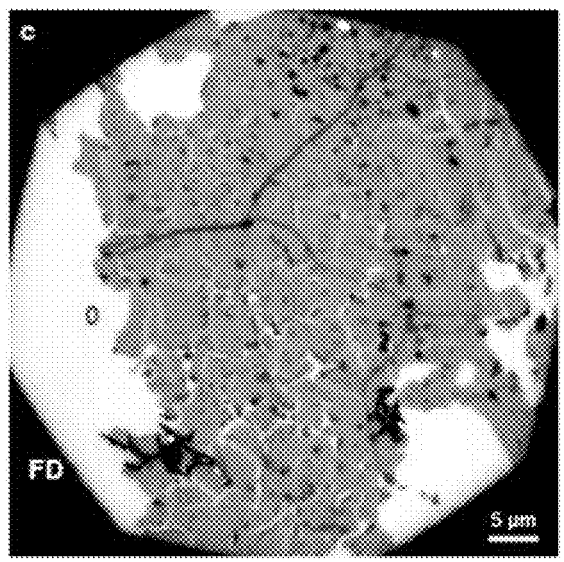
Figure 15D:
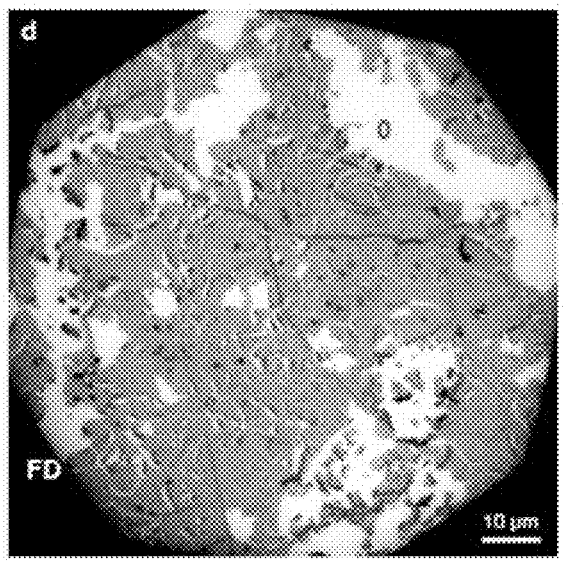
Figure 16A:
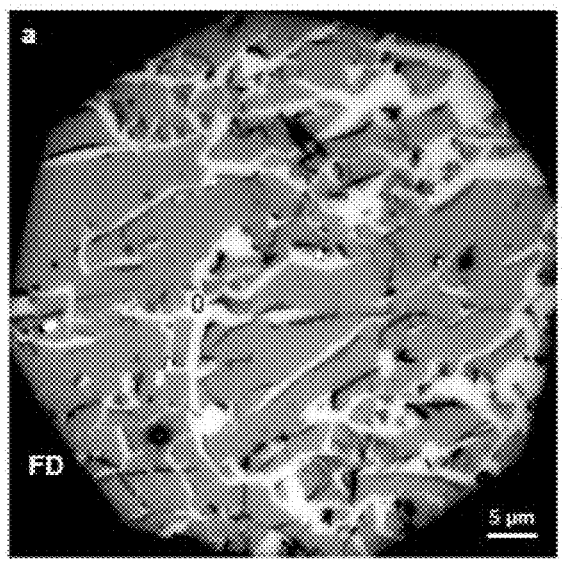
FIG. 16A-D provides additional IRM images of graphene on PET substrates. (A, B) Graphene was transferred using Scotch tapes. (C, D) Graphene was transferred using wet transfer without PMMA protection. Images were obtained using a 100× oil-immersion objective. FD: field diaphragm of the microscope. "0" marks areas with no graphene coverage.
Figure 16B:
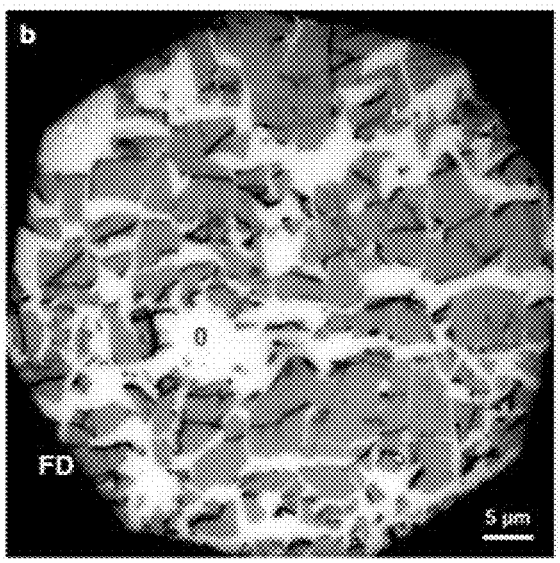
Figure 16C:
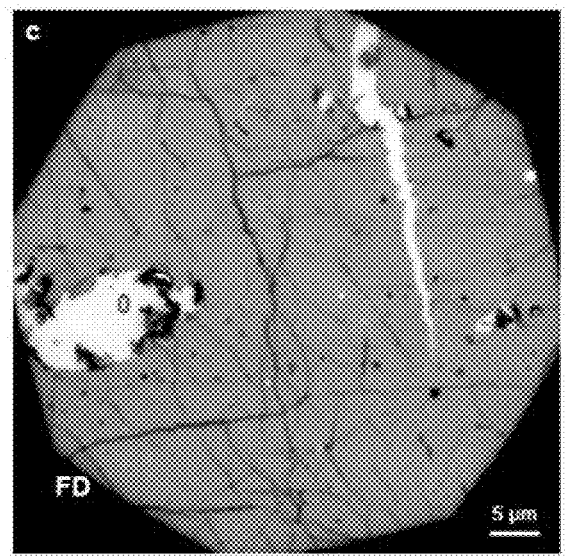
Figure 16D:
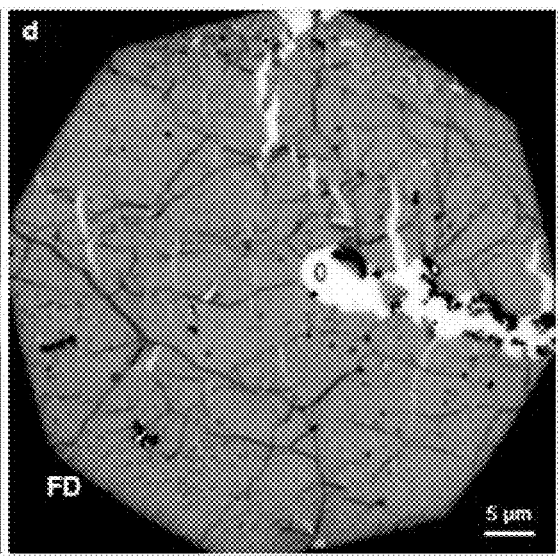
Figure 17A:
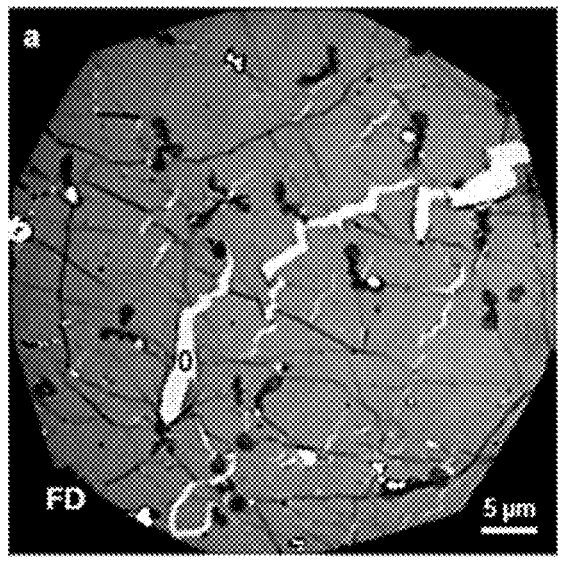
FIG. 17A-D provides additional IRM images of graphene on cellulose acetate substrates. (A, B) obtained using a 100× oil-immersion objective. (C, D) Obtained using a 60× water-immersion objective. Graphene was transferred using wet transfer without PMMA protection. FD: field diaphragm of the microscope. "0" marks areas with no graphene coverage.
Figure 17B:
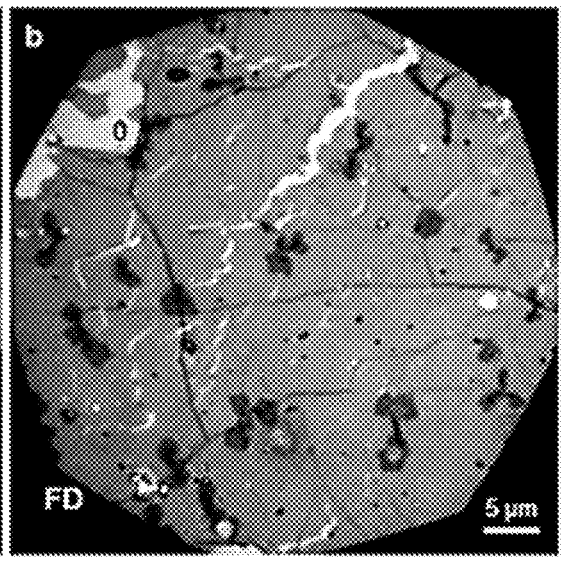
Figure 17C:
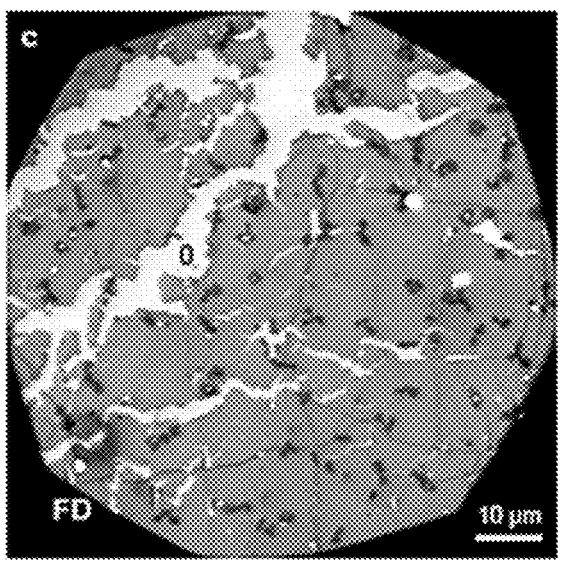
Figure 17D:
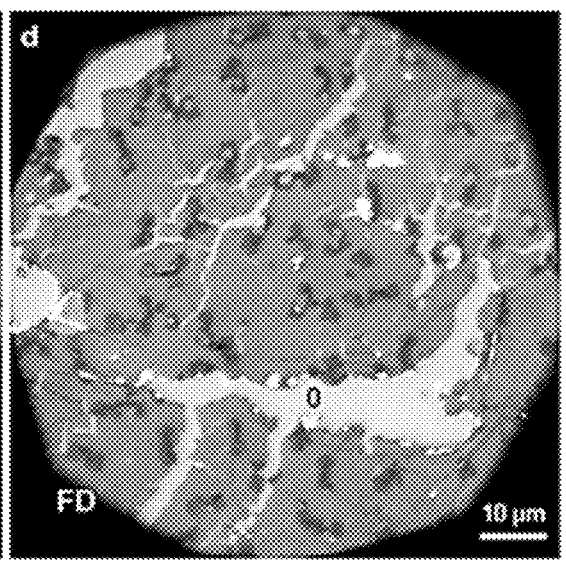

To understand the exceptional contrast that was achieved, IRM theories were acknowledged but the finite absorption of graphene and the interferences between infinite times of reflection at the substrate-graphene and graphene-medium interfaces were taken into account (see FIG. 10A). Using transfer-matrix method, it was found that the intensity of reflected light (and thus IRM signal) can be determined using Eqn. 6:

$$I = |r|^2 I_I = \left| \frac{e^{i\varphi} r_{12} + e^{-i\varphi} r_{23}}{e^{i\varphi} + e^{-i\varphi} r_{12} r_{23}} \right|^2 I_I \tag{6}$$

where $I_1$ is the intensity of incident light, $\varphi=2\pi n_2 d_2/\lambda$ is the phase change across graphene, $r_{12}=(n_1-n_2)/(n_1+n_2)$, and $r_{23}=(n_2-n_3)/(n_2+n_3)$. Here $n_1$, $n_2$, and $n_3$ are the refractive indices of the substrate, graphene, and overlying medium, respectively. $d_2=0.335$ m nm is the thickness of graphene of m layers, and $\lambda$ is the wavelength of incident light. For $\lambda=532$ nm, with glass ($n_1=1.52$) and water ($n_3=1.33$) being the substrate and the overlying medium, respectively, and using complex refractive index of graphene $n_2=2.65-1.27i$, the theoretical $C_m$ was calculated to be 31%, 34%, 36%, and 35%, for m=1-4, respectively, in good agreement with the experimental results (see FIG. 3C-D). Eqn. 6 further predicts that the achieved contrast is relatively insensitive to the wavelength, and comparable contrast without using any optical filters has been experimentally achieved (see FIG. 4).

The outstanding contrast of IRM is powerful in revealing nanoscale structures and defects in graphene. FIG. 5A shows the result on a nano-patterned graphene monolayer on glass. Excellent contrast and resolution were observed. Intensity profiles yielded ~300 nm feature widths for the finer structures, indicating that the resolution approached the diffraction limit. FIG. 5B shows a predominantly monolayer sample that was subjected to mechanical disruptions that would possibly be encountered in device fabrication. Rich features are clearly revealed, e.g., local bilayers (white arrow), tears and fold-overs ("m" arrows), and nanoscale cracks ("b" arrows) and wrinkles ("g" arrows). In comparison, conventional transmission light microscopy (see FIG. 5C) the smaller tears are overwhelmed by noise (dashed "m" arrows), and none of the nanoscale cracks or wrinkles are discernible (dashed "b" and "g" arrows).

Next, IRM with SEM and AFM (see FIG. 5D-F) was cross-examined. As the glass substrate is insulating and unsuitable for SEM, the conductivity of graphene itself was relied upon. The SEM images (see FIGS. 5E, 6, and 7) are in agreement with IRM results, but afford significantly lower contrast and SNR. Whereas bilayers and the more prominent wrinkles and cracks are visible (solid arrows), the thinner wrinkles and cracks, which are clearly resolved in IRM, are hardly observable in SEM (dashed "g" and "b" arrows). Intensity profiles indicate that the more prominent wrinkles visualized by SEM achieve SNR ~2 (see FIG. 5E inset and FIG. 7): the same wrinkles achieve SNR >30 in IRM (see FIG. 5D inset and FIG. 7).

Figure 5F:
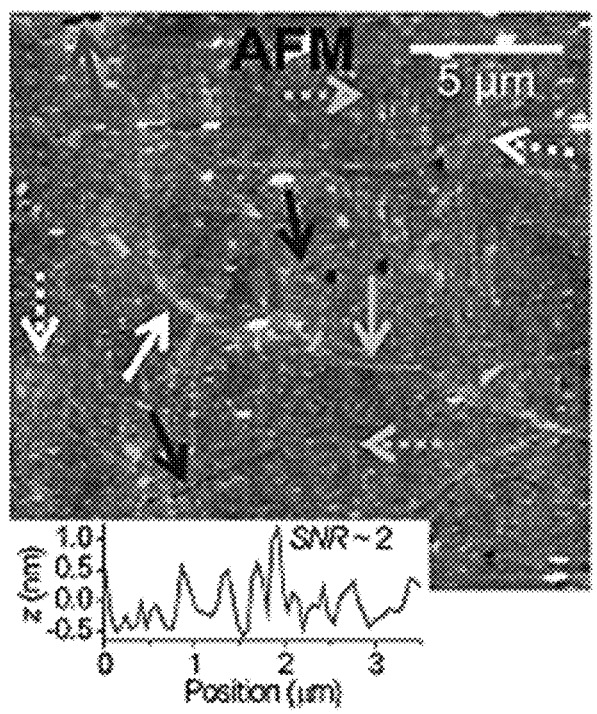

AFM also yielded structural information consistent with IRM but at much reduced contrast (see FIG. 5F and FIG. 7). Due to the relatively rough surface of glass (RMS roughness ~0.5 145 nm), features <~1 nm in height were difficult to identify. Consequently, bilayers are barely visible (white arrows), and for wrinkles, only the most prominent ones (>~1.0 nm in height) are discernible ("g" arrows). SNR <~2 was observed for the same wrinkles that achieve SNR >30 in IRM (see FIGS. 5D and F insets and FIG. 7).

In addition to structures and defects in graphene, it was noted that IRM also provides excellent visualization of nanoscale contaminants, including speckle-like debris and thread-like polymer residuals that match well with SEM and AFM results (see FIG. 5D-F and FIG. 8).

Besides outstanding contrast, IRM is further characterized by exceptional throughput, low invasive-ness, and ease of operation. Wide-field images were captured in snapshots in ~10 ms, only limited by the camera framerate. This is ~1000-times and >10 000-times faster than SEM and AFM, respectively. Moreover, IRM does not require vacuum and avoids possible sample damage due to a scanning tip or electron beam (see FIGS. 10K and L). Real-time inspection of nanoscale defects is thus readily achieved over large areas at up to 4× video-rate.

Next examined was graphene on other transparent substrates (see FIG. 10). Excellent IRM contrast of 42% and 39% (see FIGS. 10A, B, and H) is respectively observed for monolayers on quartz and $CaF_2$ substrates, which for their superior optical properties have been often employed for graphene physics and device applications. For flexible substrates, a contrast of 23%-37% was achieved for monolayer graphene on five common polymer films, namely, polychlorotrifluoroethene (Aclar), polycarbonate (PC), polyethylene terephthalate (PET), cellulose acetate (CA), and polyvinyl chloride (PVC) (see FIG. 10C-H). Nanoscale graphene structures/defects of different types were clearly visualized on all substrates. It is noted that, except Aclar, the other polymer films were noticeably attacked by solvents used to dissolve the PMMA protection layer in graphene wet-transfer. For the heat-stable PC substrate, graphene was transferred using thermal release tapes. Although a high yield was achieved, microscopic cracks were often found in the transferred graphene (see FIG. 10D). Transfer using Scotch tape led to very low yield and larger cracks (see FIG. 10E for PET). Wet transfer without PMMA protection led to low yields and frequent cracks (see FIGS. 10F and G for CA and PVC). See FIGS. 11-18 for additional data on each substrate under different preparations. By consistently achieving high contrast, IRM thus provides a way to directly characterize and compare defect levels as graphene is transferred to different potential device substrates via different procedures.

It was noted that these characterizations are difficult to achieve with alternative techniques. Due to the very large surface roughness of commercial-grade polymer films (>10 nm), AFM often does not provide useful contrast (see FIGS. 10I and J). Meanwhile, SEM provides poor contrast and causes major structural changes of the sample (see FIGS. 10K and L; and FIG. 19) due to electron beam. IRM thus uniquely provides nanoscale structural details for graphene on these substrates.

Figure 20E:
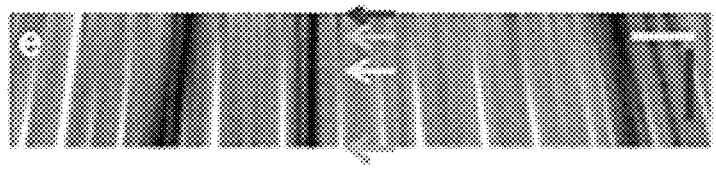
Figure 20F:
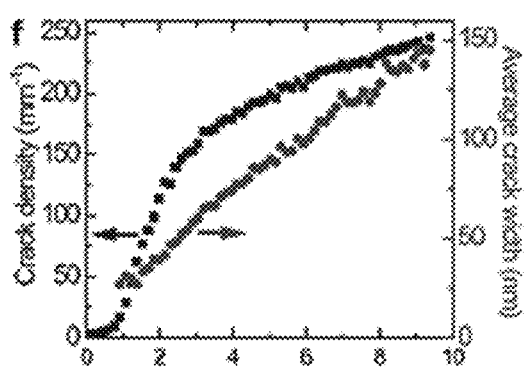
Figure 20G:
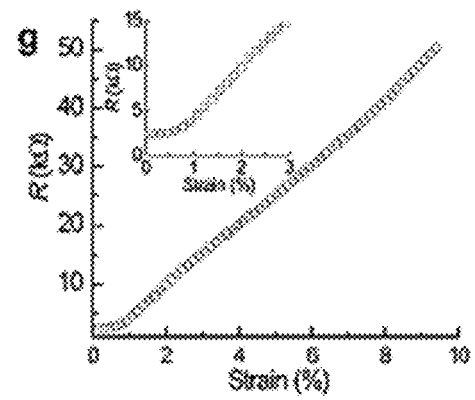
Figure 20H:
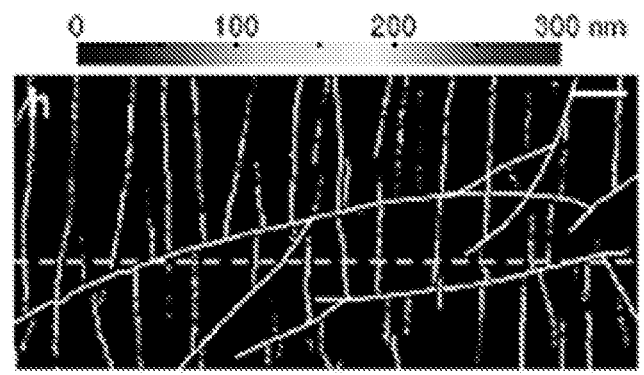
Figure 20I:

As a key demonstration of the enabling power of the technique described herein, in situ monitoring of the microscopic failure mode of graphene under strain was determined. Strain is an important performance parameter for flexible electronics. Monolayer graphene on Aclar films was subjected to uniaxial stretching, during which process concurrent IRM and electrical characterizations were performed (see FIG. 20). IRM captured the very onset of graphene failure at ~0.9% strain, where the observed emergence of nanocracks (see FIG. 20F) coincided with a sudden rise in electrical resistance (see FIG. 20G and inset). Previous bulk Raman spectroscopy studies on monolayer graphene and carbon fibers indicate mechanical failure at similar strain levels (~1.0%) although electrical measurements on multilayer devices have reported little resistance change up to 6% strain.4,5 Crack propagation ensued upon further stretching, and numerous nanocracks became readily visible in IRM at ~1.5% strain (see FIG. 20B). The rapid increase in crack density slowed down at ~4% strain, where nanocracks distributed roughly evenly across graphene at a density of ~180 mm$^{-1}$ (see FIG. 20C). Crack widening persisted throughout stretching (see FIGS. 20E, F and I); the measured average crack width, as determined from the integrated light intensity of the diffraction-limited IRM images, increased from the initial ~25 nm to ~140 nm at 9.4% strain (see FIG. 20F). Resistance increased monotonically as cracks developed and widened (see FIG. 20G). These observations bear general similarities to that reported for thin metal oxide films under strain. However, for graphene the traditional SEM approaches are unsuitable (see FIGS. 20K and L).

The IRM results reveal that for graphene, strain-induced nano-cracks are largely, but not strictly (as found in metal oxide films), perpendicular to the stretching direction. Frequent changes in crack orientation and position are observed, and wrinkles parallel to the stretching direction often block crack propagation and lead to discontinued cracks (see FIGS. 20D and H).

In contrast, wrinkles perpendicular to the stretching direction are often first flattened out during initial stretching but then evolve into cracks upon further stretching (arrows in FIG. 20A-E), suggesting mechanical instability. These results exemplify the extreme contrast and throughput of IRM. It is expected that IRM will transform how graphene and other 2D materials are characterized for both research and industrial applications.

Example 2

Sample Preparation.

Graphene samples: graphene CVD-grown on copper foils was spin-coated with a ~200 nm layer of poly(methyl methacrylate) (PMMA 495 A2, MicroChem, Newton, Mass.). The copper-graphene-PMMA stack was placed in a copper etchant solution (5% HCl+20% $FeCl_3$) to remove copper and then transferred to a fresh water bath. Water bath transfer was repeated three times to remove contaminants. A glass coverslip was subsequently used to pick the graphene-PMMA stack off of the surface of the water. The coverslip-graphene-PMMA stack was allowed to dry in air, and then PMMA was removed by immersion in acetone (1 h) followed by a rinse in isopropanol. The sample was dried with nitrogen gas. GO samples: GO solutions, as prepared by the conventional Hummers' method, were spin-coated onto glass coverslips. A droplet of diluted GO solution was placed on the surface of a coverslip and allowed to rest for 5 min. The coverslip was then spun for 60 s with an acceleration of 50 rpm/s and a final rotational speed of 3000 rpm.

Interference Reflection Microscopy (IRM).

IRM was performed on an inverted wide-field epifluorescence microscope. The Olympus IX73 microscope was configured with an UplanFl 100× oil-immersion objective (NA ~0.9 with iris diaphragm) and a standard lamp for fluorescence microscopy (U-HGLGPS). The filter cube contained a 50/50 beam splitter (Chroma 21000), a 530/10 nm band-pass filter (Chroma D532/10×) as the excitation filter, and no emission filter. The filtered light passed through the sample and was reflected at the substrate-sample-top medium interfaces (FIG. 3A). Interference between these interfaces led to wide-field IRM images, which were recorded using an Andor Zyla 4.2 sCMOS camera at 1024×1024 pixels with 16-bit depth and typical integration time of 20-500 ms. Effective pixel size was 65 nm. The microscope field diaphragm was closed down to slightly smaller than the 1024×1024 frame size to reject stray light. Prepared sample coverslips with either graphene films or GO flakes were placed on the microscope and first overlaid with a layer of water for IRM identification of suitable imaging areas. Continuous IRM recording was started, and then the water layer was replaced with a reactant solution. The reaction process was thus recorded in situ.

Data Analysis.

Collected data files contained a series of raw images 1024×1024 in size that were captured every ~100 ms (typical file size: 20-100 gigabytes). Consecutive frames were first averaged to reduce file size and further enhance signal-to-noise, so that the effective time resolution of the processed data was a few seconds, more than sufficient for the reaction dynamics in this study. The images were background-corrected and drift-corrected. Light intensity (I) of each pixel was normalized to that of the blank areas of the coverslip ($I_0$) for each frame. Measured $I_0/I$ was converted into reaction progress (local percentage of GO) through a comparison with the $I_0/I$ values of graphene and GO, as discussed in text. Local linear reaction rates (in the unit of %/min) were obtained through linear fits to the reaction progress of each pixel during different time spans as indicated. Local first-order reaction rate constants k (in the unit of min') were obtained by fitting the full time-dependent reaction progress of each pixel with a simple exponential decay.

Figure 21A:
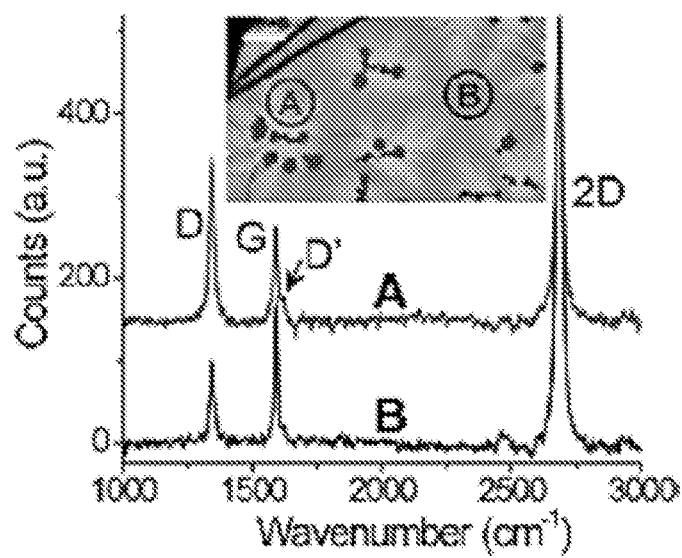
Figure 21B:
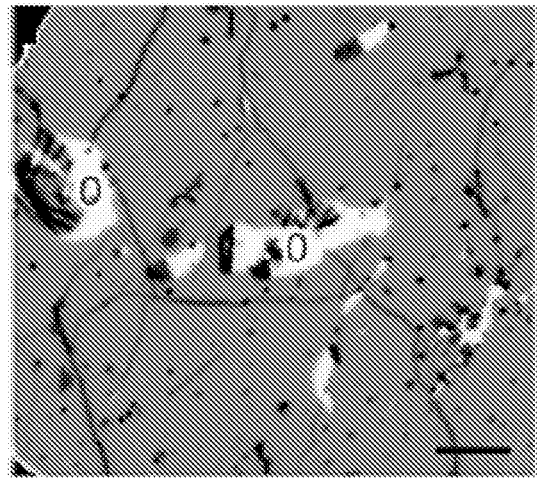

The oxidation of copper-grown graphene that was wet-transferred onto glass was examined using household bleach Clorox as the oxidant. Experimental IRM signal of the starting graphene monolayer (FIG. 21B) gave $I/I_0$=0.71, in agreement with theory. After 1 h of oxidation, micrometer-sized flower-like patterns appeared with significantly increased local intensity in IRM signal (FIG. 21C), consistent with the predicted signal change for GO (see, e.g., FIG. 3E). In comparison, conventional transmission light microscopy achieved only 2% contrast for graphene (FIG. 21E), and after reaction barely discerned the flower-like patterns as brighter areas (FIG. 21F), attributable to the much lower light absorption of GO when compared to graphene. Raman spectroscopy showed a stronger D peak, the appearance of a D' peak, and a reduced 2D peak for areas close to the flower-like patterns (FIG. 21A), indicating greater local reaction progresses. XPS results showed ~20% graphene oxidation for samples similarly prepared on a silicon substrate, consistent with the observed reaction patterns.

The excellent IRM contrast offers a possibility to quantify local reaction progress. As IRM achieves diffraction-limited spatial resolution of ~300 nm, its signal is the local average of the contrast from graphene and GO within the diffraction limited spot, and so is linearly dependent on the local fraction of GO. Thus, the measured I/I0 was directly converted into a map of the local GO percentage and thus the oxidation progress (FIG. 21D). This treatment allows for good descriptions of both reaction progress and dynamics.

The reaction progress map (FIG. 21D) revealed notable spatial heterogeneity. The reaction progress was near 100% in the central areas of each flower-like pattern, but gradually decreased to a lower extent toward the outer areas, with areas far away from the flower-like patterns remaining largely unreacted. This result suggests that the oxidation initiate from certain locations and propagates in the two-dimensional system.

Figure 21C:
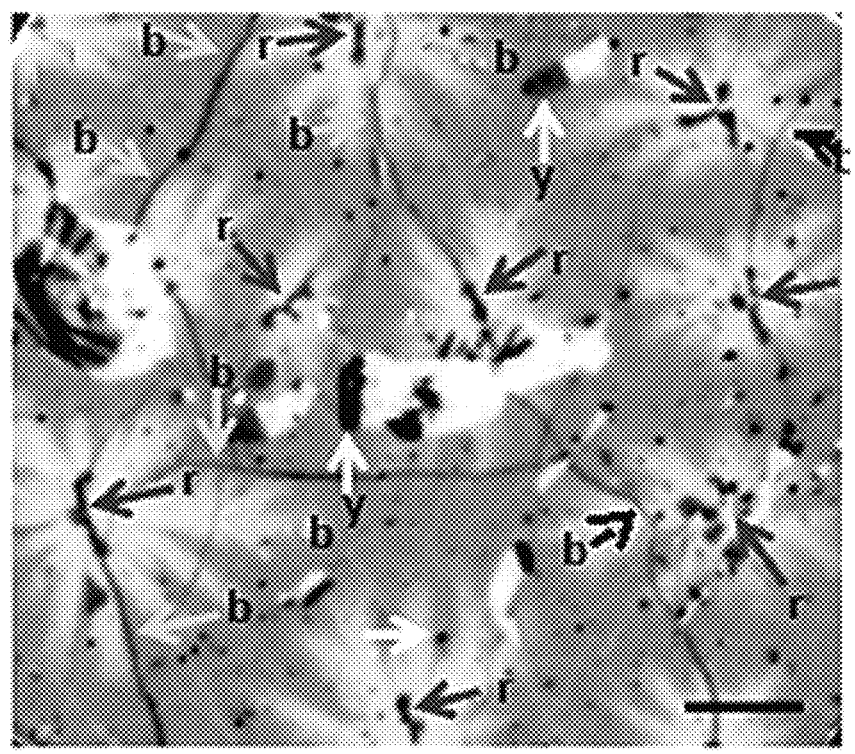
Figure 21D:
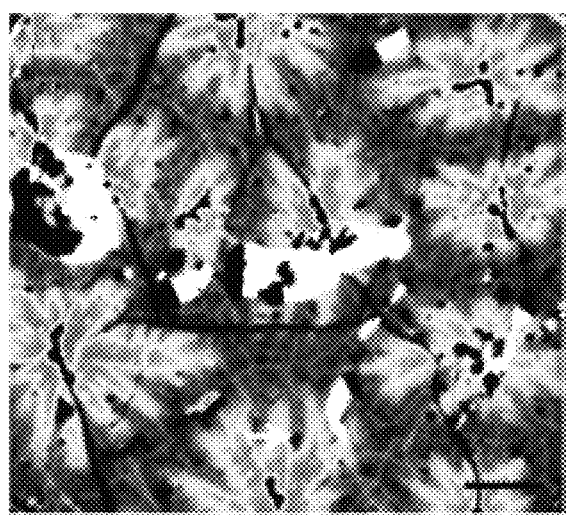
Figure 21D:
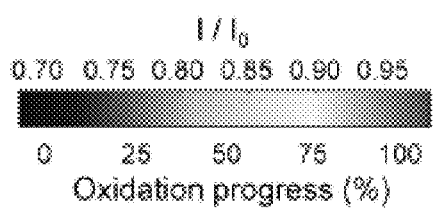

The high sensitivity of IRM for nanoscale defects enabled the identification of the reaction-initiation centers as nanoscale bilayers formed during graphene growth ("r" arrows in FIG. 21C). Stacked bilayers, e.g., those formed due to local tearing and folding-over of monolayers ("y" arrows in FIG. 21C), were not reaction centers, suggesting that it is not the presence of bilayers but rather local defects that seed the reaction hot spots. It is likely that these local defects also initiated the growth of the second layer in the first place. Edges of graphene were generally not reaction-initiation centers, an observation in line with earlier results on gas-phase oxidation of graphene. This result suggests that the oxidation of graphene is guided by different dynamics compared to electrochemical reactions of solute molecules at the graphene surface. Wrinkles in graphene were also not reaction-initiation centers. Remarkably, the more prominent wrinkles apparently blocked the propagation of reaction in the two-dimensional graphene sheet (solid "c" arrows in FIG. 21C), whereas the lesser wrinkles were less effective in blocking reaction propagation (dashed "c" arrows). AFM results indicate that the more prominent wrinkles are ~1 nm in height, whereas the lesser wrinkles visualized by IRM are difficult to probe with AFM due to surface roughness.

To understand the kinetics of how the reaction propagates in this unique two-dimensional system, in situ IRM recording of the reaction was performed in real time (FIG. 22). After 10 min of reaction, notable local oxidation was apparent close to hot spots surrounding nanoscale bilayers (FIG. 22A-B). The reaction continued at these initiation centers while propagating in two dimensions, thus forming flower-like patterns with greater reaction progress at the center (FIG. 22C). The formation of microscopic tears/cracks was also occasionally observed, attributable to tension/strain generated from the reaction. Plotting the reaction progress for different positions as a function of time (FIG. 22D for pixels 1-4 marked in FIG. 22A-C) showed sigmoidal dependence with initially low reaction rates, acceleration at different time points, and reduced rate as the reaction approaches completion.

Figure 22C:
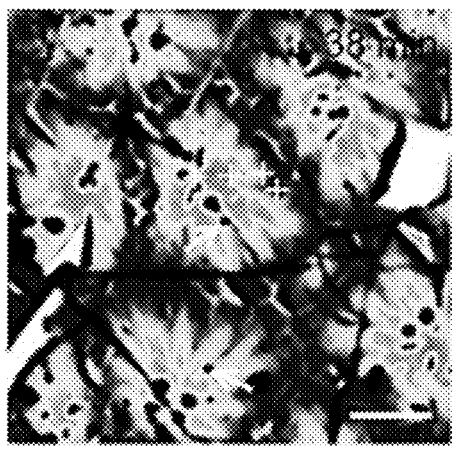
Figure 22D:
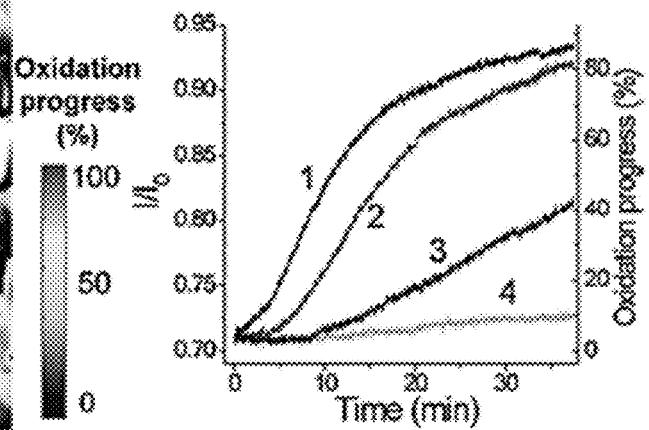
Figure 22E:
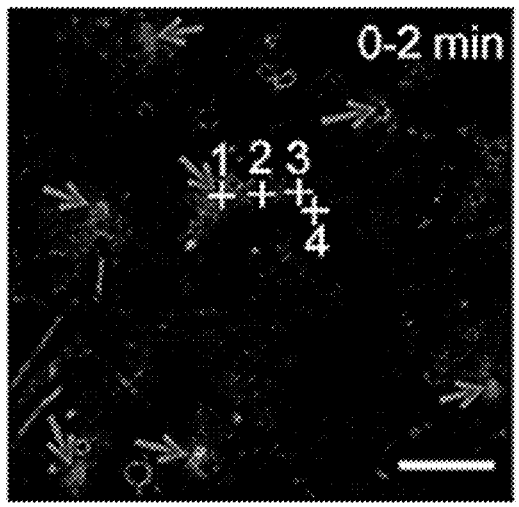
Figure 22F:
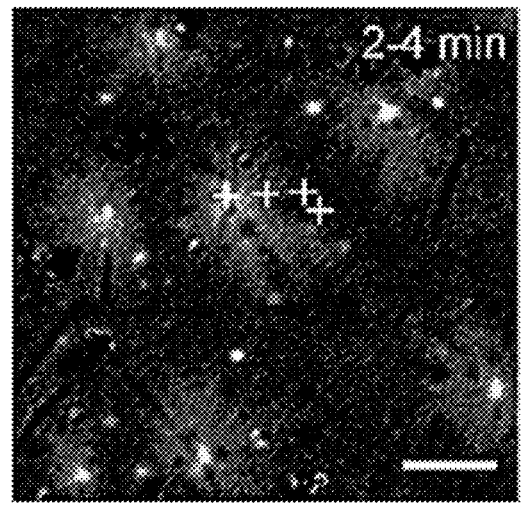
Figure 22G:
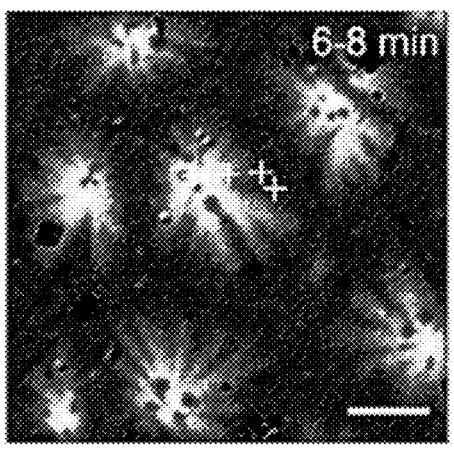

To visualize the apparent heterogeneity in reaction rate over both space and time, the local reaction rate was calculated and color-mapped at every pixel of the image from the slopes of single-pixel reaction progress curves (e.g., FIG. 22D) at different time points (FIG. 22E-H). Remarkably, at the onset of the reaction, finite (~2%/min) reaction rates were observed at highly confined local hot spots in the vicinity of local bilayers ("r" arrows in FIG. 22E; also Curve 1 in FIG. 22D). The initial reaction quickly propagated in the two dimensional system (FIG. 22F);

meanwhile, the reaction rates at the initiation centers accelerated and reached maxima of ~6%/min at 6-8 min (FIG. 22G).

Figure 22H:
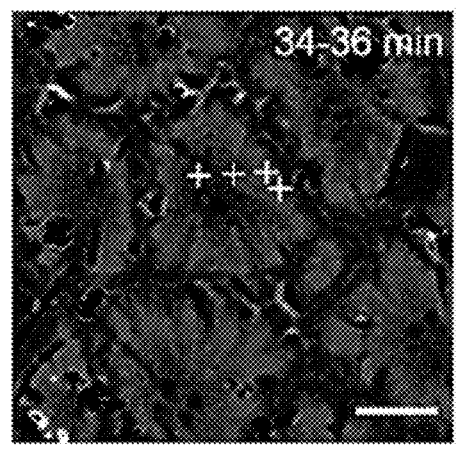
Figure 23A:
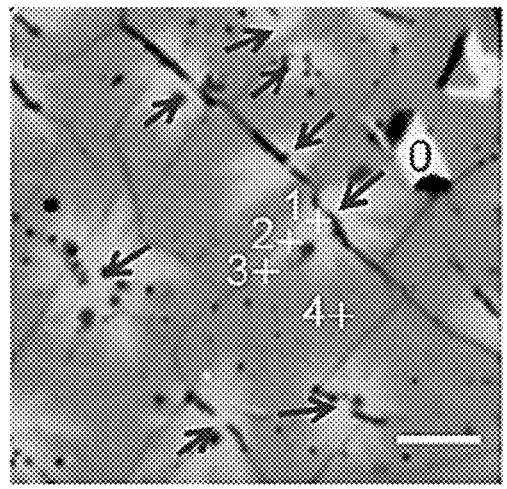
FIG. 23A-D shows reaction kinetics with a diluted oxidant. (A) IRM image of monolayer graphene after 2 h oxidation by 10% Clorox. (B) IRM monitored oxidation progression as a function of time for the four pixels marked as 1-4 in (A). (C,D) Map of local reaction rate for 24-28 min (C) and 116-120 min (D), respectively. Arrows in (A,C) point to reaction-initiation centers. Scale bars: 5 µm.
Figure 23B:
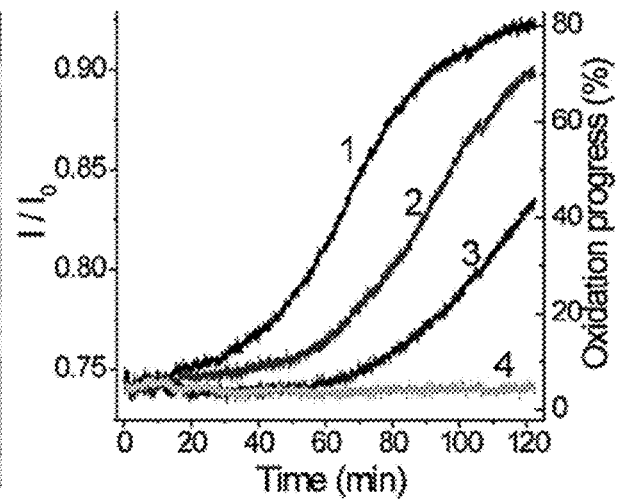
Figure 23C:
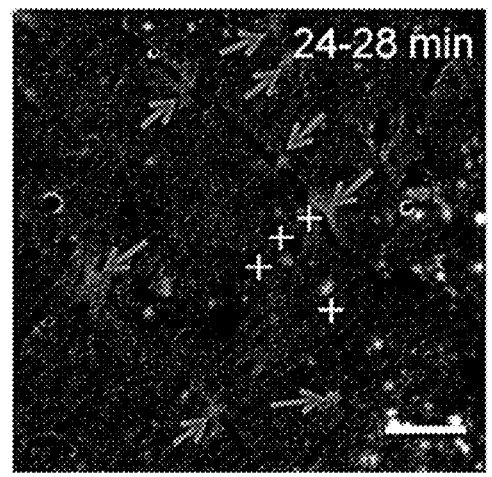
Figure 23D:
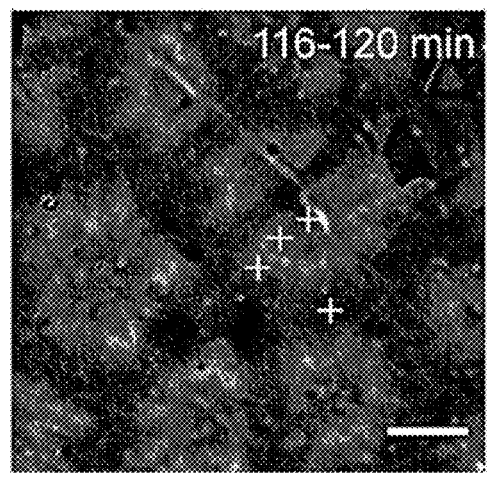

The initially slow, but later accelerating, reactions at the initiation centers are characteristic of autocatalytic reactions. Defects at bilayers apparently act as initial seeds of reaction; as the reaction progresses, more defects are locally created to promote further reaction. Areas surrounding these initiation centers initially lack defects to start the reaction, and so "wait" for periods of varied lengths (curves 2, 3 in FIG. 22D-H) for the reaction-induced defects to propagate to their locations to seed the reaction. As the locally available reaction sites are consumed, reaction rates start to drop, hence the sigmoidal local reaction progress curves and a peculiar "wavefront" of reaction rate at the edges of the flower patterns at later time points (FIG. 22H). This unique reaction propagation mechanism of the two-dimensional graphene system is reminiscent of two-dimensional crystal growth at nucleation sites, although our mechanism involves a gradual progression of local reactions and defects as opposed to rapid crystallization.

Similar reaction mechanisms were observed for diluted (10%) Clorox, but noting significantly lower reaction rates (FIG. 23). Finite reaction rates were only detected after ~20 min, again first at highly confined local hot spots in the vicinity of bilayers (FIG. 23C), indicating a much slower autocatalytic process. Slower propagation and prolonged delay time were observed across the sample (FIG. 23B-D).

Together, these results show that the oxidation kinetics of graphene is characterized by an oxidant concentration-dependent autocatalytic process that results in wave-like propagation of reaction in two dimensions.

The flower-like (as opposed to radially symmetric) patterns observed suggest strong anisotropy: The autocatalytic nature of the reaction amplifies differences in local reaction rate during radial propagation. In the IRM results, point-like nanoscale defects and wrinkles were observed that blocked the propagation of reaction and so contributed to the flower-like patterns. Other factors, including graphene crystallographic orientations and atomic structural defects, may also lead to anisotropic increases or decreases in local reaction rate.

From a different perspective, the observed wave-like, two dimensional propagation of reaction in graphene also bears a striking resemblance to chemical waves in reaction-diffusion systems; the autocatalytic oxidation mechanism makes graphene an excitable media, but here propagation of reaction is through the generation of new defects at the wavefront within the two-dimensional material as opposed to the diffusion of chemicals. Consequently, the spatial dimensions of the reaction patterns are orders of magnitude smaller.

Figure 24A:
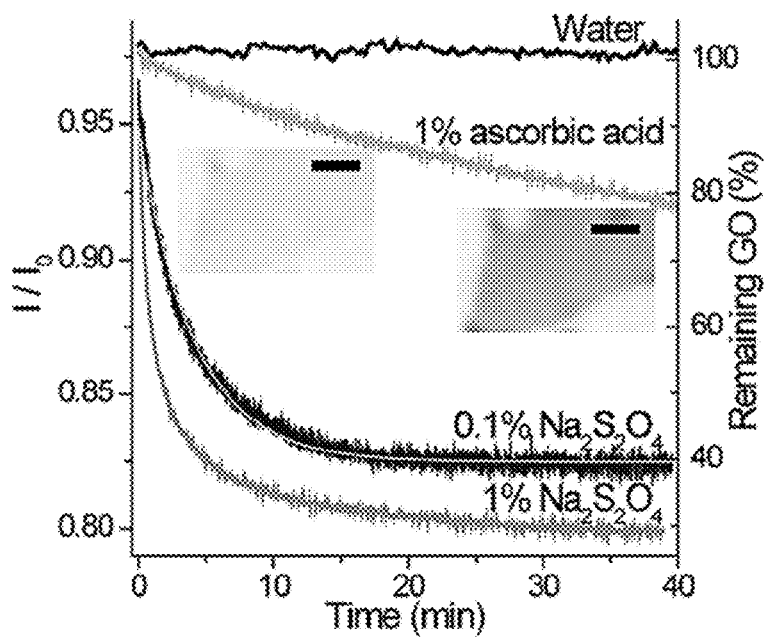
FIG. 24A-E shows in situ recording of the reduction kinetics of GO. (A) IRM signal (left axis) and the converted reaction progress (right axis) for the reduction of GO with a 1% solution of ascorbic acid and 0.1% and 1% solutions of $Na_2S_2O_4$. Result in water is shown for comparison. The 0.1% $Na_2S_2O_4$ data were drawn for two different pixels marked in (B). Other time traces are given as local (~0.1 $\mu m^2$) averages. Line is fit to the 0.1% $Na_2S_2O_4$ data to a simple exponential decay. Insets: IRM images of a GO flake before and after 40 min reduction in 1% ascorbic acid. (B) IRM images of a GO flake before (left) and after (center) 30 min reduction in 0.1% $Na_2S_2O_4$, together with the converted map of remaining GO at 30 min (right). (C) Maps of local reaction rates of the same sample at 0-2, 2-4, 4-6, 6-8, and 8-10 min, respectively. (D) Maps of the local first-order reaction rate constant k in 0.1% (left) and 1% (right) $Na_2S_2O_4$, respectively, obtained by fitting the reaction time of each pixel to a simple exponential decay. (E) Distribution of the fitted k values for reduction in 0.1% $Na_2S_2O_4$. Scale bars: 1 µm.

Next the reduction kinetics of GO were examined. Starting monolayer GO flakes, as produced by the conventional Hummers' method, exhibited typical IRM signal of $I/I_0$=0.96-0.98, in agreement with theory. A steady decrease in $I/I_0$ was observed as GO was reduced, whereas no change in $I/I_0$ was found when the top medium was water (FIG. 24A). For quantification, we again converted $I/I_0$ to reaction progress, here as the local percentage of remaining GO (right-side y-axis of FIG. 24A).

A 1% solution of ascorbic acid (vitamin C) exhibited a modest reaction rate that gradually decreased from 1%/min to 0.4%/min to reach ~20% reduction progress (~80% remaining GO) at 40 min. Spatially uniform reduction was observed for the process (FIG. 24A inset).

Figure 24B:
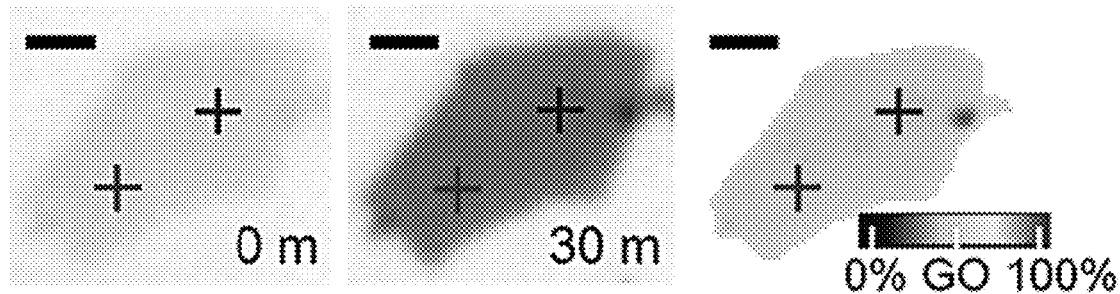
Figure 24C:
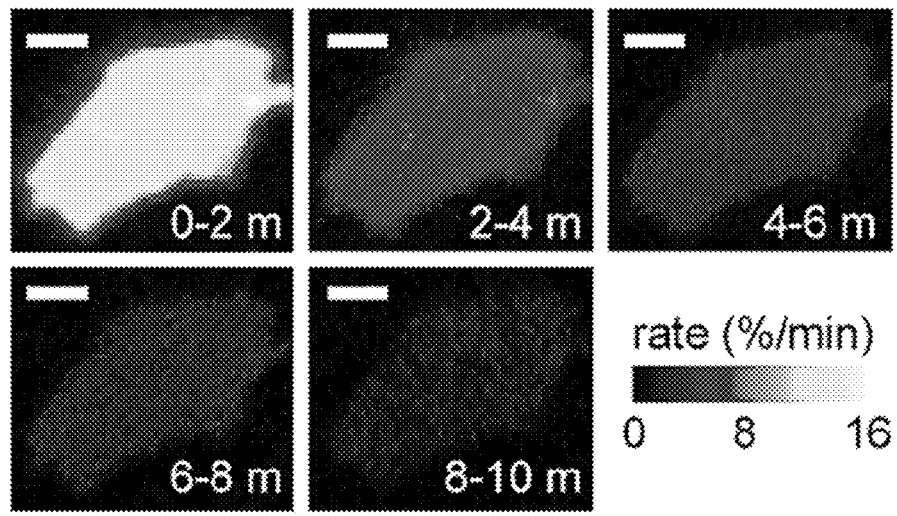

In contrast, a solution of 0.1% sodium dithionite ($Na_2S_2O_4$; also known as sodium hydrosulfite) showed a much higher initial reaction rate of >15%/min, but this rate quickly slowed down as the reduction progressed toward a limit of ~40% remaining GO (FIG. 24A). Despite this significant temporal variation in reaction rate, the reduction process is characterized by spatial homogeneity: Different locations showed near identical reaction dynamics (overlapping curves for 0.1% in FIG. 24A), and maps of the time-dependent reaction progress (FIG. 24B) and rates (FIG. 24C) were homogeneous across the sample at all time.

Figure 24D:
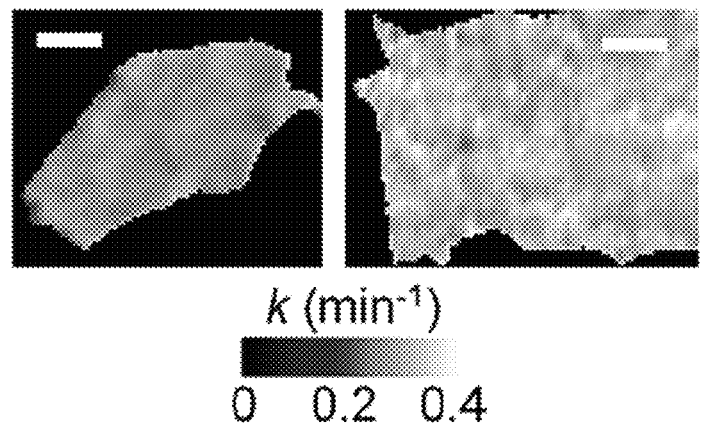
Figure 24E:
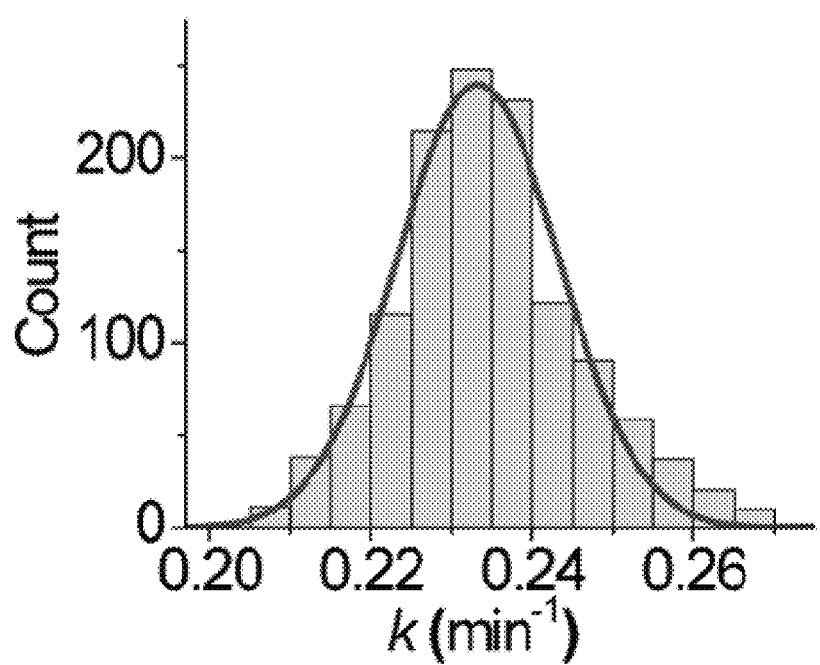

The initially fast, then quickly decelerating reaction dynamics was well fit by a simple exponential decay (FIG. 24A), suggesting a pseudo-first-order reaction mechanism in which the reaction rate is directly proportional to the remaining reaction sites in the two-dimensional GO system. By fitting an exponential decay to the reaction time trace of every pixel, the local first-order reaction rate constant k were mapped (FIG. 24D). Spatial homogeneity was again observed, with the distribution of k between pixels (FIG. 24E) within a few percent ($0.233\pm0.005$ $min^{-1}$). Reduction with 1% $Na_2S_2O_4$ showed similar, spatially homogeneous, exponential reaction dynamics with faster rates (FIG. 24A, D), and the reduction proceeded further to reach ~30% remaining GO (FIG. 24A).

Figure 25A:
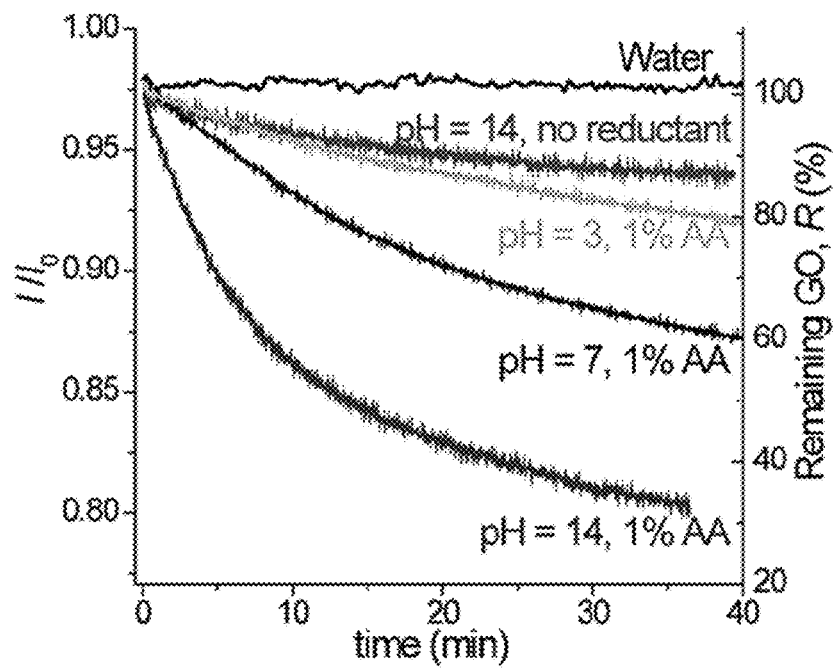
FIG. 25A-C shows in situ recording identifies pH as a key parameter in GO reduction. (A) IRM signal (left axis) and the converted reaction progress (right axis) for the reduction of GO in 1% solutions of ascorbic acid at pH 3, 7, and 14, in comparison to results in water and a pH 14 solution with no reductants added. (B) IRM mapping of the local reaction progress for pH 3, 7, and 14 at ~40 min. Scale bars: 2 µm. (C) IRM monitoring of the reduction progress of GO in 1% ascorbic acid as pH is altered from ~3 (unadjusted) to 14.
Figure 25B:
Figure 25B:
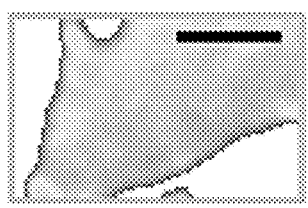
Figure 25B:
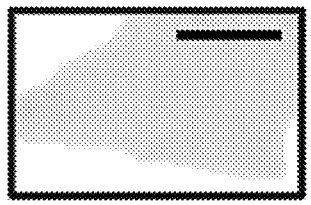
Figure 25B:
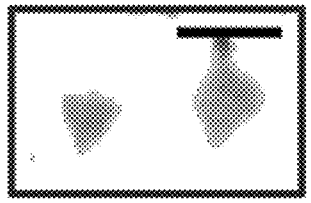

IRM was employed to probe the effects of different reaction parameters and in this process identified a strong pH dependence for the reduction of GO. An unadjusted 1% ascorbic acid solution had pH ~3. Increasing pH to 7 (neutral) and 14 (basic) led to significantly enhanced reaction rates (FIG. 25A). Spatially homogeneous reaction dynamics were observed across all samples under different conditions (FIG. 25B).

Figure 25C:
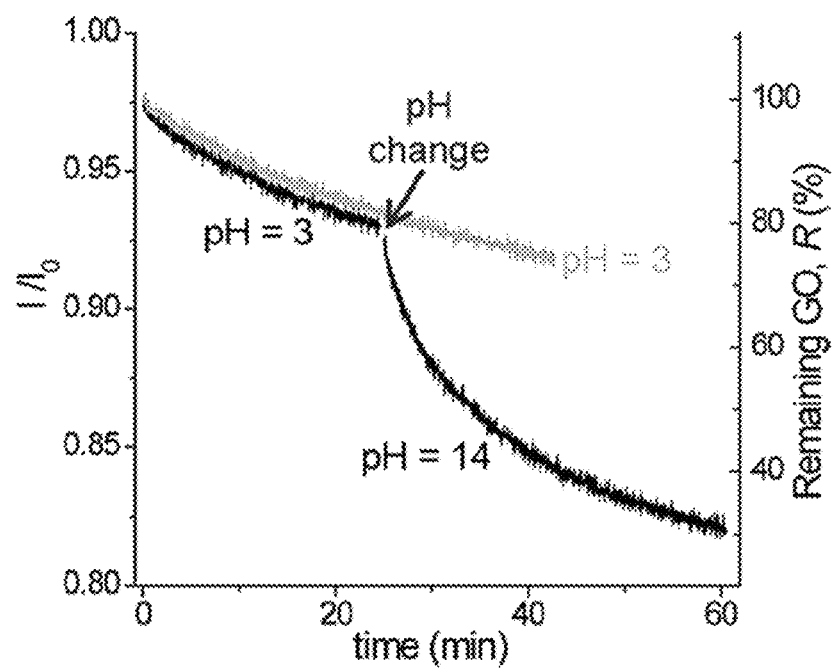

The reduction of GO by 1% ascorbic acid was monitored as pH was altered in situ from 3 to 14 (FIG. 25C). A sudden jump in reaction rate was noted, thus pinpointing pH as a key parameter of the reaction. In comparison, Raman spectroscopy only showed minor increases in D peak for reduced GO, in agreement with previous results, and no noticeable differences were found for reduction at pH=3 vs pH=14.

Previous work reported the autoreduction of GO under alkaline conditions. With IRM GO was found to be slowly reduced in a pH 14, NaOH-only solution to reach a reduction progress of ~12% at 40 min (FIG. 25A). The results thus suggest that alkaline conditions activate GO to a more reactive state, which results in both discernible autoreduction and significantly faster reactions with reductants.

A number of embodiments have been described herein. Nevertheless, it will be understood that various modifications may be made without departing from the spirit and scope of this disclosure. Accordingly, other embodiments are within the scope of the following claims.

What is claimed is:

1. A method for a direct optical visualization of graphene and its nanoscale defects comprising:
    preparing a sample comprising graphene on a transparent substrate;
    overlaying the sample with a liquid medium; and
    imaging the sample using interference reflection microscopy (IRM).

2. The method of claim 1, wherein the sample is prepared by transferring one or more layers of graphene to a transparent substrate using a wet-transfer process with polymethyl methacrylate (PMMA) protection.

3. The method of claim 2, wherein wet-transfer process with polymethyl methacrylate protection comprises:
    spin coating a layer of PMMA onto a copper foil comprising graphene;

removing the copper foil by etching to form a graphene-PMMA stack;

removing traces of ferric chloride by washing the graphene-PMMA stack with water; and transferring graphene-PMMA stack to a transparent substrate.

4. The method of claim 1, wherein the sample is prepared by transferring one or more layers of graphene to a transparent substrate using a wet-transfer process without PMMA protection.

5. The method of claim 4, wherein the wet-transfer process without PMMA protection comprises:

etching a sample comprising copper foil and graphene to remove the copper foil;

stamping the etched sample with a cleaned transparent polymer substrate; and air-drying and rinsing the stamped graphene sample with water.

6. The method of claim 1, wherein the sample is prepared by transferring one or more layers of graphene to a transparent substrate using a dry-transfer process using thermal release tape.

7. The method of claim 1, wherein the sample is prepared by transferring one or more layers of graphene to a transparent substrate using a dry-transfer process using transparent adhesive tape.

8. The method of claim 1, wherein the liquid medium is water, isopropanol, ethanol, methanol, or an organic solvent.

9. The method of claim 8, wherein the liquid medium is water.

10. The method of claim 1, wherein the IRM is performed using a conventional wide-field epifluorescence microscope equipped with a standard lamp for fluorescence microscopy and an oil-immersed objective lens.

11. The method of claim 10, wherein the IRM is configured with a 50/50 beam splitter and equipped with a 530/10 nm band pass filter.

12. The method of claim 1, wherein the intensity of reflected light is determined using the following equation:

$$I = |r|^2 I_l = \left| \frac{e^{i\varphi} r_{12} + e^{-i\varphi} r_{23}}{e^{i\varphi} + e^{-i\varphi} r_{12} r_{23}} \right|^2 I_l.$$

13. The method of claim 1, wherein the method provides one or more of the following advantages:

ultrahigh contrast for graphene (30-40% or higher contrast per graphene layer);

accurate determination of local layer numbers;

ultrahigh contrast for nanoscale structures and defects;

provides image contrasts >10-fold better than scanning electron microscopy (SEM) and atomic force microscopy (AFM);

can be used with rough and non-conductive substrates;

ultrahigh throughput that is only limited by camera frame rate;

label-free and/or non-invasive;

keeps the sample intact during imaging; and/or does not require vacuum or sophisticated optics.

14. The method of claim 13, wherein the method provides the following advantages:

ultrahigh contrast for graphene layers;

accurate determination of local layer numbers;

ultrahigh contrast for nanoscale structures and defects;

provides image contrasts >10-fold better than SEM and AFM;

can be used with rough and non-conductive substrates;

ultrahigh throughput that is only limited by camera frame rate;

label-free and/or non-invasive;

keeps the sample intact during imaging; and does not require vacuum or sophisticated optics.

15. The method of claim 1, wherein the method is used in one or more of the following applications:

ultrahigh-throughput, ultrahigh-contrast inspection of the quality of graphene for nanoscale defects over large areas;

locating and identifying graphene films or pre-patterned graphene structures during fabrication;

characterization of nanoscale defects in graphene during nanofabrication processes;

in situ characterization of how graphene-based flexible electronics fails under mechanical stresses;

in situ monitoring of the oxidation and reduction process on graphene or graphene oxide;

monitoring chemical reactions that cause changes in the index of refraction of graphene; and direct visualization of how graphene-based electronics break down due to current overload or electrostatic discharge (ESD).

16. The method of claim 1, wherein the method is used to quantify local oxidation degree of graphene with IRM contrast.

* * * * *